United States Patent
Daluge et al.

(10) Patent No.: US 7,002,012 B2
(45) Date of Patent: *Feb. 21, 2006

(54) SUBSTITUTED (1,3-BIS(CYCLOHEXYLMETHYL)-1,2,3,6-TETRAHYDRO-2,6-DIOXO-9H-PURIN-8-YI)PHENYL DERIVATIVES, THEIR PREPARATION AND THEIR USE IN THE TREATMENT OF INFLAMMATORY CONDITIONS AND IMMUNE DISORDERS

(75) Inventors: Susan Mary Daluge, Chapel Hill, NC (US); Gerald Wolberg, Cary, NC (US); Douglas Alan Livingston, Rancho Santa Fe, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 229 days.

This patent is subject to a terminal disclaimer.

(21) Appl. No.: 10/174,414

(22) Filed: Jun. 17, 2002

(65) Prior Publication Data

US 2003/0181471 A1    Sep. 25, 2003

Related U.S. Application Data

(63) Continuation of application No. 09/872,546, filed on Jun. 1, 2001, now Pat. No. 6,437,124, which is a continuation of application No. 09/367,313, filed as application No. PCT/EP98/00784 on Feb. 12, 1998, now Pat. No. 6,355,646.

(30) Foreign Application Priority Data

Feb. 14, 1997 (GB) .................................. 9703044

(51) Int. Cl.
C07D 473/06   (2006.01)
C07D 473/22   (2006.01)
A61P 29/02    (2006.01)
A61P 37/06    (2006.01)
A61K 31/522   (2006.01)

(52) U.S. Cl. .................................................. 544/271
(58) Field of Classification Search ........... 514/263.35, 514/263.34; 544/271
See application file for complete search history.

(56) References Cited

U.S. PATENT DOCUMENTS

| 4,879,296 A | 11/1989 | Daluge et al. |
| 4,968,672 A | 11/1990 | Jacobson et al. |
| 5,015,647 A | 5/1991 | Daluge et al. |
| 5,714,494 A | 2/1998 | Connell et al. |
| 6,117,878 A | 9/2000 | Linden |
| 6,355,646 B1 * | 3/2002 | Daluge et al. ......... 514/263.34 |

FOREIGN PATENT DOCUMENTS

| EP | 0 203 721 A | 12/1986 |
| EP | 0 369 744 | 5/1990 |
| EP | 0 389 282 | 9/1990 |
| EP | 0 590 919 A | 4/1994 |
| EP | 0 812 844 A | 12/1997 |
| WO | WO 92 09203 | 6/1992 |
| WO | WO 93 23401 A | 11/1993 |
| WO | WO 94 03456 A | 2/1994 |
| WO | WO 96 04280 A | 2/1996 |
| WO | WO 99 43673 | 2/1999 |
| WO | WO 00 09507 | 2/2000 |
| WO | WO 01 45703 A1 | 6/2001 |

OTHER PUBLICATIONS

Medline Medical Encyclopedia entry for Cystic fibrosis http://www.nim.nih.gov/medlineplus/ency/article/000107.htm.*

BestHealth entry for ARDS (adult respiratory distress syndrome) http://www.wfubmc.edu/besthealth/ency/article/000103prv.htm.*

The Medline Medical Encyclopediaentry for Acute gouty arthritis http://www.nim.hih.gov/medlineplus/ency/article/000422.htm.*

Columbia University College of P & S Complete Home Medical Guide entry for Arthritis Prevention http://cpmcnet.columbia.edu/texts/guide/hmg25_0006.html.*

Medline Medical Encyclopedia entry for Ankylosing spondylitis http://www.nim.nih.gov/medlineplus/ency/article/000420.htm.*

(Continued)

*Primary Examiner*—Mark L. Berch
(74) *Attorney, Agent, or Firm*—Lorie Ann Morgan

(57) ABSTRACT

A method for the prophylaxis of an inflammatory condition or immune disorder associated with infiltration of leukocytes into inflamed tissue in a subject in need thereof, which method comprises administering to the subject a therapeutically effective amount of a compound of formula (I)

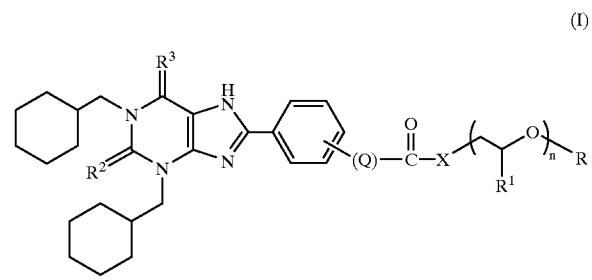

or a solvate thereof wherein:
X is —O— or —NH—;
Q is (—$CH_2$—)$_p$, (—CH=CH—)$_p$, (—C≡C—)$_p$ where p is an integer of from 0 to 4;
$R^1$ is hydrogen or methyl;
$R^2$ and $R^3$ independently represent O or S;
n is an integer of 1 to 50; and
R is hydrogen or methyl.

2 Claims, No Drawings

OTHER PUBLICATIONS

Mark Wood, "Conjunctivitis: Diagnosis and Management" http://www.jceh.co.uk/journal/30_2.asp.*

Illustrated Health Encyclopedia entry for Crohn's disease Prevention http://www.austin360.com/shared/health/adam/ency/article/000249prv.html.*

Medline Medical Encyclopedia entry for Psoriasis http://www.nim.nih.gov/medlineplus/ency/article/000434.htm.*

Medline Medical Encyclopedia entry for Eczema http://www.nlm.nih.gov/medlineplus/ency/article/000853.htm.*

NHS Direct Online Health Encyclopaedia entry for Dermatitis Prevention http://www.nhsdirect.nhs.uk/nhsdoheso/display.asp?sTopic=Dermatitis&sSection=Prevention.* podiatrychannel entry for Osteoarthritis Treatment http://www.podiatrychannel.com/osteoarthritis/treatment.shtml#prevention.*

MDAdvice.com entry for Asthma http://www.mdadvice.com/topics/asthma/info/1.htm.*

Janet R. Maurer, Lesson 23, vol. 14-Lymphangioleiomyomatosis http://www.chestnet.org/education/online/pccu/vol14/lesson23.php.*

Braun et al, Cardiovascular Research 41, 395-401 (1999).*

Roitt, "Roitt's Essential Immunology, 10$^{th}$ edition" (2001), pp. 253-254.*

Dorland's Illustrated Medical Dictionary, entry for "prophylaxis" http://www.mercksource.com/pp/us/cns/cns_hl_dorlands.jspzQzpgzEzzSzppdocszSzuszSzcommonzSzdorlandszSzdorlandzSzdmd_p_36zPzhtm downloaded from the Internet Jul. 21, 2003.*

Daluge, J. Med. Chem. 15, 171 (1972).

Braun, Cardiovascular Research 41, 395-401 (1999).

Granger, J. Leukocyte Biology 55, 662 (May, 1994).

Korthuis, J. Critical Care 9(1) 47.

* cited by examiner

SUBSTITUTED (1,3-BIS(CYCLOHEXYLMETHYL)-1,2,3,6-TETRAHYDRO-2,6-DIOXO-9H-PURIN-8-YI)PHENYL DERIVATIVES, THEIR PREPARATION AND THEIR USE IN THE TREATMENT OF INFLAMMATORY CONDITIONS AND IMMUNE DISORDERS

This Application is a continuation of U.S. patent application Ser. No. 09/872,546, filed 1 Jun. 2001 now U.S. Pat. No. 6,437,124, granted 20 Aug. 2002 which is a continuation of U.S. patent application Ser. No. 09/367,313, filed Dec. 22, 1999, now U.S. Pat. No. 6,355,646, granted 12 Mar. 2002, which was filed pursuant to 35 U.S.C. §371 as a United States National Phase Application of International Application No. PCT/EP98/00784, filed 12 Feb. 1998 and published as WO 98/35966, 20 Aug. 1998, which claims priority to Great Britain Application No. 9703044.9, filed 14 Feb. 1997.

The present invention relates to complex esters and amides of phenyl xanthine derivatives, processes for their preparation, pharmaceutical formulations comprising them, and their use in medicine, particularly in the prophylaxis and treatment of septic shock, inflammatory conditions, as well as immune disorders.

Septic shock is induced by means of a complex series of events involving many different pathways and mediators of disease response (see for instance, The Lancet, Vol. 338 (1991), p 732–739, and Annals Of Internal Medicine Vol. 115 (1991), p 457–469), including, inter alia, products of arachidonic acid metabolism and platelet aggregation.

The adhesion of circulating leukocytes to the vascular endothelium is a crucial event in the pathogenesis of inflammatory responses. Inflammatory and immune mediators can stimulate the adhesion process by increasing the adhesiveness of the leukocyte or the endothelial cell through the activation, upregulation, or induction of various adhesion molecules on the cell surface.

Anti-inflammatory drugs currently available have limited efficacy, often with side effects. Monoclonal antibodies used experimentally for anti-adhesion therapies have theoretical disadvantages for treatment of chronic diseases. Therefore, the discovery and development of small molecules which specifically block or inhibit the adhesive interactions of leukocytes and the endothelium is an attractive area of therapeutic intervention.

PCT Application No. GB 9501808 describes compounds of formula:

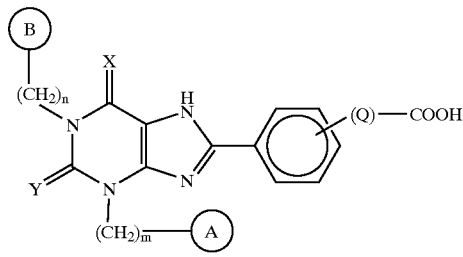

Wherein m and n are independently integers from 0 to 10;
X and Y are independently oxygen or sulphur;
(—Q—) is (—CH$_2$—)$_p$ or (—CH=CH—)$_p$ where p is an integer of from 1 to 4; and
A and B are independently methyl, branched C$_{3-6}$ alkyl, C$_{3-8}$ cycloalkyl or C$_{3-8}$ cycloalkenyl;

and salts, solvates and pharmaceutically acceptable esters and amides thereof; and their use in treatment of septic shock, allergic, and inflammatory conditions. The compounds had been found to inhibit one or more of the enzymes 5-lipoxygenase, cyclooxygenase, and lyso-PAF: acetyl-CoA acetyltransferase.

We have now surprisingly discovered a series of complex esters and amides of selected phenyl xanthine derivatives which inhibit the expression of adhesion molecules on human umbilical vein endothelial cell (HUVEC) monolayers at very low concentrations and which are therefore indicated for treatment of inflammatory conditions and immune disorders.

DETAILED DESCRIPTION OF THE INVENTION

Accordingly the present invention provides a compound of formula (I):

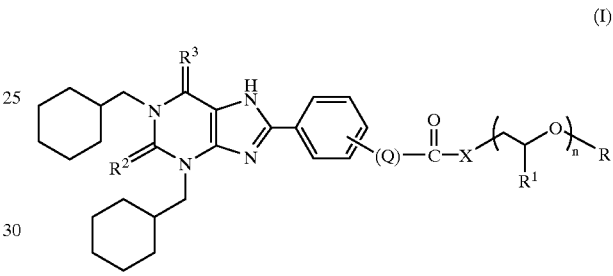

or a solvate thereof wherein:
X is —O— or —NH—;
Q is (—CH$_2$—)$_p$, (—CH=CH—)$_p$, (—C≡C—)$_p$ where p is an integer of from 0 to 4;
R$^1$ is hydrogen or methyl;
R$^2$ and R$^3$ independently represent O or S.
n is an integer of 1 to 50; and
R is hydrogen or methyl.

According to a further aspect, the present invention provides a compound of formula (I) as defined above wherein X is —O— or —NH— and R$^1$ is H; of these, compounds wherein n is an integer of 8 to 20 are preferred, and those wherein n is an integer of 8 to 15 are more preferred.

Conveniently R$^3$ represents O and R$^2$ represents O or S but more preferably R$^3$ and R$^2$ both represent O.

According to a further aspect of the invention, P preferably represents 0 or 1.

According to a further aspect, the present invention provides a compound of formula (I) as defined above wherein Q is (—CH=CH—)$_p$.

Preferably the

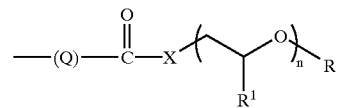

substituent is attached to the phenyl ring in the para position.

The invention also includes mixtures of compounds of formula (I) in any ratio, for example wherein n varies within the same sample.

A particular subgroup of compounds is of formula 1a

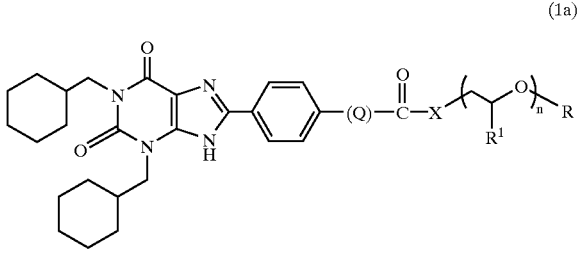

or a solvate thereof wherein:
X is —O— or —NH—;
Q is (—CH$_2$—)$_p$ or (—CH=CH—)$_p$ where
P is an integer from 1 to 4;
R$^1$ is hydrogen or methyl
n is an integer of 1 to 50; and
R is hydrogen or methyl.
Particularly preferred compounds of the invention include
(E)-4-(1,3-Bis(cyclohexylmethyl)-1,2,3,6-tetrahydro-2,6-dioxo-9H-purin-8-yl)cinnamic Acid Decaethylene Glycol Methyl Ether Ester;

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester;

(E)-3-[1,3-Bis(cyclohexylmethyl)-1,2,3,6-tetrahydro-2,6-dioxo-9H-purin-8-yl]cinnamic Acid Nonaethylene Glycol Methyl Ether Ester;

(E)-4-[1,3-Bis(cyclohexylmethyl)-1,2,3,6-tetrahydro-2,6-dioxo-9H-purin-8-yl]cinnamic acid Nonaethylene Glycol Methyl Ether Amide and (E)-4-[1,3-Bis(cyclohexylmethyl)-1,2,3,6-tetrahydro-2,6-dioxo-9H-purin-8-yl]benzoic acid Nonaethylene Glycol Methyl Ether Ester or a solvate thereof.

The compounds of the present invention are capable of existing as geometric and optical isomers. All such isomers, individually and as mixtures, are included within the scope of the present invention. Where Q contains a double bond, compounds in the form of the E-geometric isomers are preferred.

As mentioned hereinbefore, compounds of formula (I) and solvates thereof, have use in the prophylaxis and treatment of inflammatory conditions and immune disorders, as demonstrated hereinafter in the biological assays in which representative compounds of the present invention have been shown to be active.

Examples of inflammatory conditions or immune disorders are those of the lungs, joints, eyes, bowel, skin, and heart; particularly those associated with the infiltration of leucocytes into inflamed tissue. Conditions of the lung include asthma, adult respiratory distress syndrome, bronchitis and cystic fibrosis (which may additionally or alternatively involve the bowel or other tissue(s)). Conditions of the joint include rheumatoid arthritis, rheumatoid spondylitis, osteoarthritis, gouty arthritis and other arthritic conditions. Inflammatory eye conditions include uveitis (including iritis) and conjunctivitis. Inflammatory bowel conditions include Crohn's disease, ulcerative colitis and distal proctitis. Skin diseases include those associated with cell proliferation, such as psoriasis, eczema and dermatitis (whether or not of allergic origin). Conditions of the heart include coronary infarct damage. Other inflammatory conditions and immune disorders include tissue necrosis in chronic inflammation, endotoxin shock, smooth muscle proliferation disorders (for example, restenosis following angioplasty), and tissue rejection following transplant surgery.

Accordingly, the present invention provides a method for the prophylaxis or treatment of an inflammatory condition or immune disorder in a mammal, such as a human, which comprises administration of a therapeutically effective amount of a compound of formula (I), or a pharmaceutically acceptable solvate thereof. The present invention further provides a method for the prophylaxis or treatment of septic shock in a mammal, such as a human, which comprises administration of a therapeutically effective amount of a compound of formula (I), or a pharmaceutically acceptable solvate thereof.

In the alternative, there is also provided a compound of formula (I), or a pharmaceutically acceptable solvate thereof for use in medical therapy; particularly, for use in the prophylaxis or treatment of an inflammatory condition or immune disorder in a mammal, such as a human. The present invention further provides a compound of formula (I), or a pharmaceutically acceptable solvate thereof for use in the prophylaxis or treatment of septic shock.

The amount of a compound of formula (I) or pharmaceutically acceptable solvate thereof, which is required to achieve the desired biological effect will depend on a number of factors such as the use for which it is intended, the means of administration, and the recipient. A typical daily dose for the treatment of septic shock, for instance, may be expected to lie in the range of 0.005 mg/kg–100 mg/kg, preferably 0.5–100 mg/kg, and most preferably 0.5–20 mg/kg. This dose may be administered as a single unit dose or as several separate unit doses or as a continuous infusion. An intravenous dose may be expected to lie in the range of 0.0025 mg/kg to 200 mg/kg and would typically be administered as an infusion. Similar dosages would be applicable for the treatment of other disease states. For administration to the lungs of a subject by aerosol an amount of the compound should be used sufficient to achieve concentrations on the airway surface liquid of the subject of about 2 to 1000 µmol.

Thus, in a further aspect of the present invention, there are provided pharmaceutical compositions comprising, as active ingredient, a compound of formula (I) or a pharmaceutically acceptable salt or solvate thereof, together with at least one pharmaceutical carrier or recipient. These pharmaceutical compositions may be used in the prophylaxis and treatment of conditions such as septic shock, inflammatory conditions, and immune disorders. The carrier must be pharmaceutically acceptable to the recipient and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredients. If desired other physiologically active ingredients may also be incorporated in the pharmaceutical compositions of the invention.

Possible formulations include those suitable for oral, sublingual, buccal, parenteral (for example subcutaneous, intramuscular, or intravenous), rectal, topical including transdermal, intranasal and inhalation administration. Most suitable means of administration for a particular patient will depend on the nature and severity of the condition being treated and on the nature of the active compound, but where possible, iv administration is preferred for the treatment of septic shock, for instance. For the treatment of a condition such as asthma, however, oral or inhalation, would be the preferred route of administration.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavoured base, such as sugar and acacia or tragacanth and pastilles comprising the active compound in an innert base, such as gelatine and glycerine or sucrose acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethyleneglycols, alcohols, and combinations thereof. The active ingredient is typically present in such formulations at a concentration of from 0.1 to 15% w/w.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions are typically prepared by dissolving the active ingredient in saline to which cyclodextrin has been added.

Suitable formulations for administration by inhalation include fine particle dusts or mists which may be generated by means of various types of metered dose pressurised aerosols, nebulisers, or insufflators.

For pulmonary administration via the mouth, the particle size of the powder or droplets is typically in the range 0.5–10 $\mu$m, preferably 1–5 $\mu$m, to ensure delivery into the bronchial tree. For nasal administration, a particle size in the range 10–500 $\mu$m is preferred to ensure retention in the nasal cavity.

Metered dose inhalers are pressurised aerosol dispensers, typically containing a suspension or solution formulation of the active ingredient in a liquefied propellant. During use, these devices discharge the formulation through a valve adapted to deliver a metered volume, typically from 10 to 150 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane an mixtures thereof The formulation may additionally contain one or more co-solvents, for example, ethanol surfactants, such as oleic acid or sorbitan trioleate, antioxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavouring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

Therefore, according to a further aspect of the present invention, there is provided the use of a compound of formula (I) or a pharmaceutically acceptable solvate thereof in the preparation of a medicament for the prophylaxis or treatment of an inflammatory condition or immune disorder.

Compounds according to the invention can be made according to any suitable method of organic chemistry. Therefore, according to a further aspect of the invention, there is provided a process for preparing the compounds of formula (I), or solvates thereof which comprises reacting the compound of formula (II)

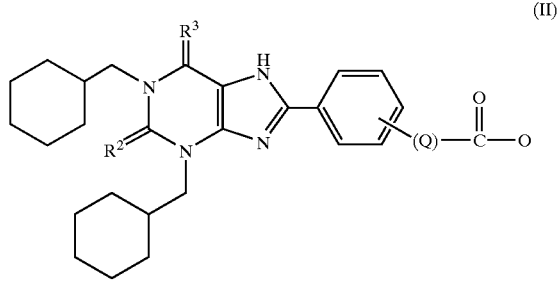

(II)

or an activated derivative thereof with a compound of formula (III)

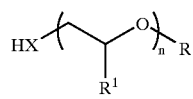

wherein Q, X, R¹, R, R² and R³ and n are as hereinbefore defined.

and optionally converting the compound of formula (I) so formed to a different compound of formula (I) or to a corresponding solvate.

When X is oxygen, the esterification may be effected by standard methods, for example using an acid catalyst and, optionally, an inert solvent such as toluene, benzene, or a xylene. Suitable acid catalysts include mineral acids; for example, sulphuric acid, hydrochloric acid, and phosporic acid; and organic acids; for example, methanesulphonic acid, or toluenesulphonic acid. The esterification is typically carried out at elevated temperature, for example, 50–150° C., preferably with removal of the water formed by distillation.

Where X is oxygen or —NH—, the reaction may be effected by first preparing an activated derivative of the compound of formula (II). Suitable activated derivatives include activated esters or acid halides and may either be isolated before reaction with the compound of formula (III) or prepared in situ. Particularly useful activated esters of the compound of formula (II) are acylimidazoles which are readily prepared by reaction of the compound of formula (II) with N,N¹-carbonyldiimidazole.

Conversion of an activated derivative of the compound of formula (II) to a compound of formula (I) may be effected in an inert solvent, optimally in the presence of a non-nucleophilic base, such as potassium t-butoxide, sodium hydride, or a non-nucleophilic organic base, such as 1,8-diazabicylo [5.4.0] undec-7-ene.

The compound of formula (II) may be prepared as described in PCT application No. GB 9501808.

Compounds of formula (III) are commercially available or may be prepared by literature methods. For example, R. A. Bartsch et al, J. Org. Chem. 1989, 54: 857–860 and J. M. Harris, Macromol. J. Sci. Rev. Polymer Phys. Chem. 1985, C25 (3): 325–373, and S. Zalopsky, Bioconjugate Chem. 1995, 6: 150–165.

Alternatively, compounds of formula (I) may be prepared by condensation of a compound of formula (IV)

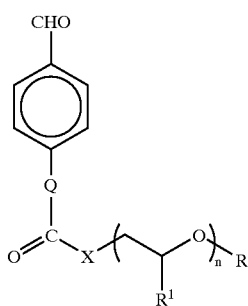

(IV)

or an acetal derivative thereof, wherein Q, X, R¹, n and R are as hereinbefore defined, with 1,3-bis(cyclohexylmethyl)-5,6-diaminouracil (which may be prepared as described in the Examples). The condensation is suitably carried out in a polar solvent at non-extreme temperature as described in PCT Application No. GB9501808.

Compounds of formula (IV) may be prepared by coupling a compound of formula (III) with the appropriate carboxylic acid. Methods for effecting this coupling and for preparing the carboxylic acid are described in PCT Application No. GB9501808.

Conversion of a compound of formula (I) to a solvate thereof may be effected by standard methods known to a person skilled in the art.

The invention will now be described by way of illustration only, by the following examples:

REFERENCE EXAMPLE

Example 1

(E)-4-[1,3 Bis(cyclohexylmethyl)-1,2,3,6-tetrahydro-2,6-dioxo-9H-purin-8-yl]cinnamic acid (a) 1,3-Bis(cyclohexylmethyl)urea A mixture of cyclohexanemethylamine (Aldrich, 68.66 g) and 5 N sodium hydroxide (Fisher, 200 ml) was stirred vigorously with cooling (−10° C.) while a solution of phosgene (30.0 g) in toluene (600 ml) was added rapidly. After stirring for 20 minutes, the resulting mixture was filtered and the precipitated solid was washed with water (~1500 ml) and dried (0.5 Torr) to give 1,3-bis(cyclohexylmethyl)urea as white powder (72.72 g, 95%), m.p. 150–152° C.; $^1$H-NMR (DMSO-$d_6$) δ: 5.74 (br t, J=5.8 Hz, 2, 2 NH), 2.81 (t, J=6.3 Hz, 4, 2 NCH$_2$), 1.62, 1.25, and 0.85 (all m, 22, 2 cyclohexyl).

Anal. Calcd for $C_{15}H_{28}N_2O$: C, 71.38; H, 11.18; N, 11.10. Found: C, 71.22; H, 11.17; N, 11.15.

(b) 6-Amino-1,3-bis(cyclohexylmethyl)uracil

Cyanoacetic acid (Aldrich, 21.0 g) was dissolved in acetic anhydride (260 ml). This solution was added to 1,3-bis (cyclohexylmethyl)urea (from step (a), 54.5 g) and the solution maintained at 80° C. for 2 h under nitrogen. Volatiles were removed in vacuo and the residual oil dried by evaporation of portions of 10% water-ethanol (3×400 ml). The residual solids were dissolved in ethanol (600 ml)-water(300 ml) at 80° C. with adjustment of the pH to 10 by addition of 10% aqueous sodium carbonate. The hot solution was diluted with water (75 ml) and cooled to ambient temperature. The colorless crystals which formed were filtered off, washed with water (3×500 ml) and dried at 0.5 Torr to give 6-amino-1,3-bis(cyclohexylmethyl)uracil (64.98 g, 94%), m.p. 138–141° C.; $^1$H-NMR (DMSO-$d_6$) δ: 6.73 (br s, 2, NH$_2$), 4.63 (s, 1, H-5), 3.67 (d, J=7.3 Hz, 2, NCH$_2$), 3.57 (d, J=7.3 Hz, 2, NCH$_2$), 1.55 and 1.09 (both m, 22, 2 cyclohexyl).

Anal. Calcd for $C_{18}H_{29}N_3O_2 \cdot H_2O$: C, 64.07; H, 9.26; N, 12.45. Found: C, 63.98; H, 9.27; N, 12.48.

(c) 6-Amino-1,3-bis(cyclohexylmethyl)-5-nitrosouracil

6-Amino-1,3-bis(cyclohexylmethyl)uracil (from step (b), 25.0 g) was dissolved in glacial acetic acid (440 ml), water (440 ml) and ethanol (440 ml) at reflux. To this solution was added sodium nitrite (5.65 g). The resulting mixture was stirred as it cooled slowly to ambient temperature. The lavender precipitate was filtered off, washed with 1:1 water-ethanol and dried to give 6-amino-1,3-bis(cyclohexylmethyl)-5-nitrosouracil as light purple crystals (23.46 g, 86%), m.p. 240–243° C. dec with effervescence; $^1$H-NMR (DMSO-$d_6$) δ: 13.23 (br s, 1, =NOH), 9.00 (br s, 1, =NH), 3.73 (br t, J=6.86, 4, 2 NCH$_2$), 2.0–1.6 and 1.7–1.1 (both m, total 22, 2 cyclohexyl).

Anal. Calcd for $C_{18}H_{28}N_4O_3$: C, 62.05; H, 8.10; N, 16.08. Found: C, 62.13; H, 8.12; N, 16.03.

(d) (E)-4-[1,3 Bis(cyclohexylmethyl)-1,2,3,6-tetrahydro-2,6-dioxo-9H-purin-8-yl]cinnamic acid The title compound was prepared from 1,3-bis(cyclohexylmethyl)-5,6-diaminouracil by the method of J. Perutmattam, Syn. Commun. 1989, 19:3367–3370. 1,3-Bis(cyclohexylmethyl)-5,6-diaminouracil was freshly prepared by shaking a mixture of 6-amino 1,3-bis(cyclohexylmethyl)-5-nitrosouracil (from step (c), 5.00 g) in methanol (250 ml)-water (25 ml) with 10% palladium on carbon (0.50 g) under hydrogen (50 psi) on a Parr shaker for 2 h. The catalyst was filtered off (Celite) and the colorless filtrate was concentrated to 25 ml. 4-Formylcinnamic acid (Aldrich, 2.53 g, 14.35 mmol) was added to this solution of 1,3-bis(cyclohexylmethyl)-5,6-diaminouracil and the resulting yellow mixture was concentrated and the residual yellow solid dried by evaporation of several portions of absolute ethanol. The resulting yellow powder (Schiff base intermediate) was stirred in dimethoxyethane (115 ml) with iodine (4.0 g) at 60° C. (oil bath) for 20 h. A saturated aqueous solution of sodium thiosulfate was added to the warm reaction mixture until complete decolorization of iodine resulted. The pale yellow precipitate was filtered off, washed with water, and dried at 0.5 Torr to give (E)-4-[1,3 bis(cyclohexylmethyl)-1,2,3,6-tetrahydro-2,6-dioxo-9H-purin-8-yl]cinnamic acid as a pale yellow powder (6.73 g, 91%), m.p.>300° C. Such samples were further purified by dissolving them in 1N aqueous sodium hydroxide, filtering the resulting hazy solution through Celite, and acidifying the clear filtrate with hydrochloric acid. The resulting precipitate was filtered and washed with water to give title compound as a pale yellow powder, m.p.>300° C.; $^1$H-NMR (DMSO-$d_6$) δ: 13.80 and 12.40 (both br m, 1 each, $CO_2H$ and NH), 8.12 (d, J=8.3 Hz, 2, 2 phenyl CH), 7.84 (d, J=8.4 Hz, 2, 2 phenyl CH), 7.64 (d, J=16.0 Hz, 1, CH=), 6.64 (d, J=16.0 Hz, 1, CH=), 3.93 (d, J=7.0 Hz, 2, $CH_2N$), 3.79 (d, J=6.8 Hz, 2, $CH_2N$), 2.0–1.4 and 1.3–0.85 (both br m, 22 total, 2 cyclohexyl).

Anal. Calcd for $C_{28}H_{34}N_4O_4$: C, 68.55; H, 6.99; N, 11.42. Found: C, 68.45; H, 6.98; N, 11.48.

SYNTHETIC EXAMPLES

Example 2

(E)-4-(1,3-Bis(cyclohexylmethyl)-1,2,3,6-tetrahydro-2,6-dioxo-9H-purin-8-yl)cinnamic Acid Triethylene Glycol Methyl Ether Ester Triethylene glycol, monomethyl ether (Aldrich, 80.0 g) was dried by evaporation of portions of xylenes (3×50 ml) under a stream of $N_2$ at 125° C. (E)-4-[1,3 Bis(cyclohexylmethyl)-1,2,3,6-tetrahydro-2,6-dioxo-9H-purin-8-yl]cinnamic acid (from step (d) example 1, 4.00 g) was then added to the glycol, and the mixture was further dried by evaporation of xylenes (40 ml). Sulfuric acid (0.41 g) was added to the reaction mixture, which was then heated to 190° C. Xylenes were added in 50 ml portions to replace that being distilled off. After 2 h, the reaction mixture was treated with additional sulfuric acid (0.2 g). After an additional 3 h at 140° C., during which time the xylenes were continuously replaced, the reaction mixture was allowed to cool to ambient temperature, which caused a great deal of solid to precipitate from the brown solution. The mixture was diluted with chloroform (200 ml), and washed with water (4×50 ml). The organic layer was dried (sodium sulfate) and concentrated to afford a yellow solid, which was chromatographed on silica gel. The title compound eluted with 1–4% methanol in ethyl acetate, and was recrystallized from ethyl acetate by the addition of hexanes to provide title compound as a white powder (3.2 g, 62%), m.p. 189–192° C.; $^1$H-NMR (DMSO-$d_6$) δ: 8.16 (d, J=8.0 Hz, 2, 2 phenyl CH), 7.88 (d, J=8.3 Hz, 2, 2 phenyl CH), 7.70 (d, J=16.1 Hz, 1, CH=), 6.77 (d, J=16.1 Hz, 1, CH=), 4.28 (m, 2, $CO_2CH_2$), 3.92 (d, J=6.8 Hz, 2, $CH_2N$), 3.78 (d, J=6.8 Hz, 2, $CH_2N$), 3.68 (m, 2, $CH_2O$), 3.6–3.5 (m, 6, 3 $CH_2O$), 3.40 (2, $CH_2O$), 3.23 (s, 3, $CH_3$), 2.0–1.5 and 1.3–0.9 (both br m, 22 total, 2 cyclohexyl).

Anal. Calcd for $C_{35}H_{48}N_4O_7$: C, 66.02; H, 7.60; N, 8.80 Found: C, 65.91; H, 7.58; N. 8.76.

Example 3

(E)-4-(1,3-Bis(cyclohexylmethyl)-1,2,3,6-tetrahydro-2,6-dioxo-9H-purin-8-yl)cinnamic Acid Polyethylene Glycol (n=7.2) Methyl Ether Ester A slurry of (E)-4-[1,3 bis(cyclohexylmethyl)-1,2,3,6-tetrahydro-2,6-dioxo-9H-purin-8-yl]cinnamic acid (from step (d) example 1, 0.50 g) in poly(ethyleneglycol) monomethyl ether (Aldrich, average molecular weight 350, 21 g, dried by evaporation of toluene prior to use) containing sulfuric acid (51 mg) was stirred at 1 Torr for 15 min. The yellow reaction mixture was then stirred at 190° C. (oilbath) and 1 Torr for 3 h, during which time the solids dissolved, leaving a brown solution. After cooling to ambient temperature, the dark solution was poured onto water (100 ml). The aqueous mixture was stirred for 1.75 h before being extracted with dichloroethane (3×30 ml). The combined extracts were then dried (sodium sulfate), and concentrated to a waxy solid, which was chromatographed on C-18 reverse phase silica gel (EM Separations LiChroprep RP-18). The column was, eluted with a gradient from 10% water-methanol to neat methanol; crude product eluted in neat methanol as a yellow waxy solid, which was slurried in water (25 ml). The water was then evaporated under vacuum to provide the title compound as yellow waxy solid (620 mg, 61%), m.p. 147–154° C.; $^1$H-NMR (DMSO-$d_6$) δ: 8.15 (d, J=8.1 Hz, 2, 2 phenyl CH), 7.88 (d, J=8.2 Hz, 2, 2 phenyl CH), 7.70 (d, J=16.0 Hz, 1, CH=), 6.77 (d, J=16.0 Hz, 1, CH=), 4.28 (m, 2, $CO_2CH_2$), 3.91 (d, J=7.0 Hz, 2, $CH_2N$), 3.78 (d, J=7.1 Hz, 2, $CH_2N$), 3.68 (m, 2, $CH_2O$), 3.6–3.38 (m, ca 25, ca 12.5 $CH_2O$), 3.22 (s, 3, $CH_3$), 2.0–1.5 and 1.3–0.9 (both br m, 22 total, 2 cyclohexyl).

Anal. Calcd for $C_{29}H_{36}N_4O_4$ $(C_2H_4O)_{7.2}$·0.6 $H_2O$: C, 62.56 H, 8.00; N, 6.69. Found: C, 62.62; H, 8.01; N, 6.69.

Example 4

(E)-4-(1,3-Bis(cyclohexylmethyl)-1,2,3,6-tetrahydro-2,6-dioxo-9H-purin-8-yl)cinnamic Acid Tetraethylene Glycol Methyl Ether Ester (E)-4-(1,3-Bis(cyclohexylmethyl)-1,2,3,6-tetrahydro-2,6-dioxo-9H-purin-8-yl)cinnamic acid polyethylene glycol (n=7.2) methyl ether ester (from example 3, 2.0 g) was separated into its components via repeated chromatography employing a Chromatotron (Harrison Research). Portions of the ester mixture (250–350 mg) in ethyl acetate were applied to 1 mm thick silica plates that had been preequilibrated with hexanes. The plates were then eluted with a gradient from 5–20% ethyl acetate in hexanes. Fractions containing discrete oligomers were isolated separately, and identical fractions from the various plates were pooled and concentrated. All mixed fractions were combined and rechromatographed. In this manner (E)-4-(1,3-bis(cyclohexylmethyl)-1,2,3,6-tetrahydro-2,6-dioxo-9H-purin-8-yl)cinnamic acid tetraethylene glycol methyl ether ester was obtained as a white powder (43 mg), m.p. 171–174° C.; $^1$H-NMR (DMSO-$d_6$) δ: 8.18 (d, J=8.4 Hz, 2, 2 phenyl CH), 7.91 (d, J=8.4 Hz, 2, 2 phenyl CH), 7.72 (d, J=16.1 Hz, 1, CH=), 6.80 (d, J=16.1 Hz, 1, CH=), 4.30 (m, 2, CO$_2$CH$_2$), 3.94 (d, J=7.1 Hz, 2, CH$_2$N), 3.80 (d, J=7.1 Hz, 2, CH$_2$N), 3.71 (m, 2, CH$_2$O), 3.58–3.42 (m, 12, 6 CH$_2$O), 3.24 (s, 3, CH$_3$), 2.0–1.5 and 1.3–0.9 (both br m, 22 total, 2 cyclohexyl).

Anal. Calcd for $C_{29}H_{36}N_4O_4$ $(C_2H_4O)_4$.0.6 H$_2$O: C, 64.25; H, 7.75; N, 8.10 Found: C,64.11; H,7.56; N, 8.07.

Example 5

(E)-4-(1,3-Bis(cyclohexylmethyl)-1,2,3,6-tetrahydro-2,6-dioxo-9H-purin-8-yl)cinnamic Acid Pentaethylene Glycol Methyl Ether Ester Chromatographic separation of (E)-4-(1,3-bis(cyclohexylmethyl)-1,2,3,6-tetrahydro-2,6-dioxo-9H-purin-8-yl)cinnamic acid polyethylene glycol (n=7.2) methyl ether ester (from example 3, 2.0 g) into its components as described in example 4 provided the title compound as a yellow waxy solid (92 mg), m.p. 166–167° C.; $^1$H-NMR (DMSO-$d_6$) δ: 8.18 (d, J=8.2 Hz, 2, 2 phenyl CH), 7.91 (d, J=8.2 Hz, 2, 2 phenyl CH), 7.72 (d, J=16.0 Hz, 1, CH=), 6.79 (d, J=16.1 Hz, 1, CH=), 4.30 (m, 2, CO$_2$CH$_2$), 3.94 (d, J=7.0 Hz, 2, CH$_2$N), 3.80 (d, J=7.0 Hz, 2, CH$_2$N), 3.70 (m, 2, CH$_2$O), 3.60–3.40 (m, 16, 8 CH$_2$O), 3.24 (s, 3, CH$_3$), 2.0–1.5 and 1.3–0.9 (both br m, 22 total, 2 cyclohexyl).

Anal. Calcd for $C_{29}H_{36}N_4O_4$ $(C_2H_4O)_5$.0.15 H$_2$O: C, 64.38; H, 7.80; N, 7.70 Found: C, 64.44; H, 7.90; N, 7.57.

Example 6

(E)-4-(1,3-Bis(cyclohexylmethyl)-1,2,3,6-tetrahydro-2,6-dioxo-9H-purin-8-yl)cinnamic Acid Hexaethylene Glycol Methyl Ether Ester Chromatographic separation of (E)-4-(1,3-bis(cyclohexylmethyl)-1,2,3,6-tetrahydro-2,6-dioxo-9H-purin-8-yl)cinnamic acid polyethylene glycol (n=7.2) methyl ether ester (from example 3, 2.0 g) into its components as described in example 4 provided the title compound as a yellow waxy solid (170 mg), m.p. 160–162° C.; $^1$H-NMR (DMSO-$d_6$) δ: 8.18 (d, J=8.2 Hz, 2, 2 phenyl CH), 7.91 (d, J=8.2 Hz, 2, 2 phenyl CH), 7.74 (d, J=16.0 Hz, 1, CH=), 6.79 (d, J=16.1 Hz, 1, CH=), 4.30 (m, 2, CO$_2$CH$_2$), 3.93 (d, J=6.8 Hz, 2, CH$_2$N), 3.80 (d, J=7.2 Hz, 2, CH$_2$N), 3.70 (m, 2, CH$_2$O), 3.60–3.40 (m, 20, 10 CH$_2$O), 3.24 (s, 3, CH$_3$), 2.0–1.5 and 1.3–0.9 (both br m, 22 total, 2 cyclohexyl).

Anal. Calcd for $C_{29}H_{36}N_4O_4$ $(C_2H_4O)_6$.0.20 H$_2$O: C, 63.74; H, 7.88; N, 7.25 Found: C, 63.69; H, 7.92; N, 7.34.

Example 7

(E)-4-(1,3-Bis(cyclohexylmethyl)-1,2,3,6-tetrahydro-2,6-dioxo-9H-purin-8-yl)cinnamic Acid Heptaethylene Glycol Methyl Ether Ester Chromatographic separation of (E)-4-(1,3-bis(cyclohexylmethyl)-1,2,3,6-tetrahydro-2,6-dioxo-9H-purin-8-yl)cinnamic acid polyethylene glycol (n=7.2) methyl ether ester (from example 3, 2.0 g) into its components as described in example 4 provided the title compound as a yellow waxy solid (105 mg), m.p. 154–156° C.; $^1$H-NMR (DMSO-$d_6$) δ: 8.18 (d, J=8.4 Hz, 2, 2 phenyl CH), 7.91 (d, J=8.4 Hz, 2, 2 phenyl CH), 7.73 (d, J=16.0 Hz, 1, CH=), 6.79 (d, J=16.1 Hz, 1, CH=), 4.30 (m, 2, CO$_2$CH$_2$), 3.94 (d, J=7.0 Hz, 2, CH$_2$N), 3.80 (d, J=7.2 Hz, 2, CH$_2$N), 3.70 (m, 2, CH$_2$O), 3.60–3.40 (m, 24, 12 CH$_2$O), 3.24 (s, 3, CH$_3$), 2.0–1.5 and 1.3–0.9 (both br m, 22 total, 2 cyclohexyl).

Anal. Calcd for $C_{29}H_{36}N_4O_4$ $(C_2H_4O)_7$.0.25 H$_2$O: C, 63.18; H, 7.95; N, 6.85 Found: C, 63.15; H, 7.97; N, 6.93.

Example 8

(E)-4-(1,3-Bis(cyclohexylmethyl)-1,2,3,6-tetrahydro-2,6-dioxo-9H-purin-8-yl)cinnamic Acid Octaethylene Glycol Methyl Ether Ester Chromatographic separation of (E)-4-(1,3-bis(cyclohexylmethyl)-1,2,3,6-tetrahydro-2,6-dioxo-9H-purin-8-yl)cinnamic acid polyethylene glycol (n=7.2) methyl ether ester (from example 3, 2.0 g) into its components as described in example 4 provided the title compound as a yellow waxy solid (120 mg), m.p. 150–151° C.; $^1$H-NMR (DMSO-$d_6$) δ: 8.18 (d, J=8.4 Hz, 2, 2 phenyl CH), 7.91 (d, J=8.6 Hz, 2, 2 phenyl CH), 7.73 (d, J=16.0 Hz, 1, CH=), 6.79 (d, J=16.1 Hz, 1, CH=), 4.30 (m, 2, CO$_2$CH$_2$), 3.94 (d, J=7.0 Hz, 2, CH$_2$N), 3.80 (d, J=7.2 Hz, 2, CH$_2$N), 3.70 (m, 2, CH$_2$O), 3.60–3.40 (m, 28, 14 CH$_2$O), 3.24 (s, 3, CH$_3$), 2.0–1.5 and 1.3–0.9 (both br m, 22 total, 2 cyclohexyl).

Anal. Calcd for $C_{29}H_{36}N_4O_4$ $(C_2H_4O)_8$.0.25 H$_2$O: C, 62.73; H, 8.01; N, 6.50 Found: C, 62.65; H, 8.10; N, 6.56.

Example 9

(E)-4-(1,3-Bis(cyclohexylmethyl)-1,2,3,6-tetrahydro-2,6-dioxo-9H-purin-8-yl)cinnamic Acid Decaethylene Glycol Methyl Ether Ester (a) Decaethylene Glycol Monomethyl Ether Potassium t-butoxide (Aldrich, 95%, 239.24 g) was added in portions over a 1.25 h period to a solution of triethylene glycol monomethyl ether (Aldrich, 300 ml, 1.9 mol) and 1,2-bis(2-chloroethoxy)ethane (Aldrich, 500 g). The reaction temperature was maintained at 16–20° C. during the addition (icebath). After removal of the cooling bath, the reaction temperature reached 30° C. before cooling to ambient temperature. The reaction mixture was stirred at ambient temperature for 2 h, followed by 18 h at 110° C., before volatiles were removed (19 Torr, 110–125° C.). The viscous residue was then diluted with toluene (1.7 L), and filtered through Celite. Toluene was distilled off such that the pot temperature never exceeded 165° C., and methyl hexaethylene glycol chloride was then isolated via fractional distillation of the light brown residue (0.6 Torr, 155–190° C., 95.78 g, 16%).

Potassium t-butoxide (Aldrich, 95%, 39.0 g) was added to a solution of tetraethylene glycol (Aldrich, 412.7 g) and methyl hexaethylene glycol chloride from above (95.8 g) at 18° C. over a 25 min period (ice/acetone bath). The reaction mixture was then stirred at 120° C. overnight. The pH was adjusted to 7 by the addition of hydrochloric acid (12 N, 11.7 ml), and volatiles were removed (0.48 Torr, up to 185° C.). The residual dark oil was diluted with toluene (250 ml), and treated with calcium chloride (38.1 g). After stirring for 18 h, the mixture was filtered through Celite and concentrated to a dark oil (102 g), which was fractionally distilled to provide decaethylene glycol monomethyl ether as an amber oil (64.4 g, 45%).

An analytical sample was obtained via chromatography on silica gel, eluting with 4% methanol in chloroform to provide a colorless oil; $^1$H-NMR (DMSO-d$_6$) δ: 4.58 (t, J=5.5 Hz, 1, OH), 3.58–3.38 (m, 40, 20 OCH$_2$), 3.24 (s, 3, OCH$_3$).

Anal. Calcd for C$_{21}$H$_{44}$O$_{11}$: C, 53.37; H, 9.38. Found: C, 53.09; H, 9.47.

(b) (E)-Methyl 4-(dimethoxymethyl)cinnamate

4-Formylcinnamic acid dimethyl acetal (Cleeland, Jr., et al., U.S. Pat. No. 3,969,373) (20.00 g) and anhydrous potassium carbonate (12.44 g) were stirred in anhydrous N,N-dimethylformamide (189 ml) for 5 minutes. Methyl iodide (12.8 g) was added and the resulting mixture was stirred vigorously with gentle heating (oil bath at 40° C.) for 18 h. Volatiles were evaporated in vacuo and the residue partitioned between hexanes (400 ml) and water (100 ml). The hexanes layer was dried (magnesium sulfate) and evaporated to give (E)-methyl 4-(dimethoxymethyl)cinnamate as a pale yellow oil (18.98 g, 89%), $^1$H-NMR (DMSO-d$_6$) consistent with structure.

Anal. Calcd for C$_{13}$H$_{16}$O$_4$: C, 66.09; H, 6.83. Found: C, 65.96; H, 6.86.

(c) 4-Formylcinnamic Acid Decaethylene Glycol Methyl Ether Ester

A solution of methyl 4-(dimethoxymethyl)cinnamate (from step (b), 4.96 g), decaethylene glycol monomethyl ether (from step (a), 14.87 g), and titanium(IV) isopropoxide (Aldrich, 1.05 ml) was stirred at 110° C. under high vacuum for 18 h. The resulting black oil was then cooled to 35° C., treated with hydrochloric acid (1 N, 24.5 ml), and extracted with toluene (3×100 ml). The combined extracts were concentrated to a dark oil, which was chromatographed on silica gel. The title compound eluted with 10% methanol in chloroform as a yellow oil (4.60 g, 34%), $^1$H-NMR (DMSO-d$_6$) δ: 10.54 (s, 1, CHO), 7.98 (m, 4, 4 phenyl CH), 7.76 (d, J=16 Hz, 1, CH=), 6.88 (d, J=16 Hz, 1, CH=), 4.31 (m, 2, CO$_2$CH$_2$), 3.70 (m, 2, OCH$_2$), 3.51 (m, 36, 18 OCH$_2$), 3.25 (s, 3, OCH$_3$).

Anal. Calcd for C$_{31}$H$_{50}$O$_{13}$·0.65 H$_2$O: C, 537.96; H, 8.05. Found: C, 57.95; H, 7.95.

(d) (E)-4-(1,3-Bis(cyclohexylmethyl)-1,2,3,6-tetrahydro-2,6-dioxo-9H-purin-8-yl)cinnamic Acid Decaethylene Glycol Methyl Ether Ester The title compound was prepared from 1,3-bis(cyclohexylmethyl)-5,6-diaminouracil by the method of J. Perutmattam, Syn. Commun. 1989, 19:3367–3370. In the manner of step (d) of example 1, 6-amino 1,3-bis(cyclohexylmethyl)-5-nitrosouracil (from step (c) example 1, 2.00 g) was converted to 1,3-bis(cyclohexylmethyl)-5,6-diaminouracil, which was then combined with 4-formylcinnamic acid decaethylene glycol monomethyl ether ester (from step (c), 3.62 g) in ethanol (50 ml). The resulting yellow mixture was concentrated, and the residual yellow semi-solid was dried by evaporation of several portions of absolute ethanol. The resulting yellow semi-solid (Schiff base intermediate) was then stirred in dimethoxyethane (60 ml) with iodine (1.60 g, 6.31 mmol) at 50° C. (oilbath) for 18 h. Sufficient saturated aqueous sodium thiosulfate solution was added to the warm reaction mixture to effect complete decolorization of iodine. The aqueous mixture was concentrated to a volume of 20 ml, diluted with water (50 ml), and extracted with chloroform (4×50 ml). The combined organic layers were then dried (magnesium sulfate) and concentrated to give an oily solid, which was chromatographed on silica gel. The title compound eluted in 6% methanol in chloroform as a yellow oil (3.6 g), which was partitioned between chloroform (150 ml) and water (50 ml). The organic layer was concentrated, and the resulting oil was precipitated from dichloromethane by the addition of hexanes to provide title compound as a yellow powder, which was then washed with hexanes and dried under vacuum at 56° C. (2.57 g, 47%), m.p. 143–145° C. $^1$H-NMR (DMSO-d$_6$) δ: 8.16 (d, J=8.4 Hz, 2, 2 phenyl CH), 7.88 (d, J=8.5 Hz, 2, 2 phenyl CH), 7.70 (d, J=16.0 Hz, 1, CH=), 6.78 (d, J=16.0 Hz, 1, CH=), 4.29 (m, 2, CO$_2$CH$_2$), 3.92 (d, J=7.1 Hz, 2, CH$_2$N), 3.78 (d, J=7.1 Hz, 2, CH$_2$N), 3.69 (t, J=4.6 Hz, 2, CH$_2$O), 3.60–3.35 (m, 36, 18 CH$_2$O), 3.23 (s, 3, CH$_3$), 2.0–1.5 and 1.3–0.9 (both br m, 22 total, 2 cyclohexyl).

Anal. Calcd for C$_{49}$H$_{76}$N$_4$O$_{14}$: C, 62.28; H, 8.10; N, 5.93. Found: C, 62.14; H, 8.06; N, 6.02.

Example 10

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester (a) Nonaethylene Glycol Monomethyl Ether A mixture of hexaethylene glycol (Aldrich, 100 g) and benzyl bromide (Aldrich, 12 g) in aqueous sodium hydroxide (50% (w/w), 80 ml) was stirred at 100° C. (oil bath) under nitrogen for 2 h. The reaction mixture was then cooled to ambient temperature, diluted with water to a total volume of 500 ml, and extracted with diethyl ether (200 ml) to remove dibenzylated product. Sodium chloride (100 g) was added to the aqueous layer, which was extracted further with diethyl ether (6×100 ml). These ether extracts were combined, dried (sodium sulfate), and concentrated to give hexaethylene glycol monobenzyl ether as an oil (25 g, 20% based on glycol), $^1$H-NMR (CDCl$_3$) δ: 7.30 (m, 5, 5 phenyl CH), 4.53 (s, 2, benzyl CH$_2$), 3.69–3.54 (m, 22, 11 OCH$_2$), 3.06 (br s, 3, OH and CH$_2$O).

A solution of toluene sulfonyl chloride (Aldrich, 38 g) and triethylene glycol monomethyl ether (Aldrich, 16.4 g) in dry pyridine (150 ml) was stirred at 0° C. (icebath) for 4 h, followed by 18 h at ambient temperature. The solution was then poured onto ice water (500 ml) and extracted with diethyl ether extracts were combined, washed with hydrochloric acid (3 N) and water, dried (sodium sulfate), and concentrated to provide triethylene glycol methyl tosyl ether as a colorless oil (20.0 g, 62% based on glycol), $^1$H-NMR (CDCl$_3$) δ: 7.75 (d, J=8.0 Hz, 2, 2 phenyl CH), 7.30 (d, J=8.1 Hz, 2, 2 phenyl CH), 4.11 (t, J=4.8 Hz, 2, CH$_2$OS), 3.65–3.41 (m, 10, 5 CH$_2$O), 3.32 (s, 3, CH$_3$O) and 2.40 (s, 3, benzylic CH$_3$).

A solution of hexaethylene glycol monobenzyl ether from above (22.3 g) in anhydrous THF (100 ml) was added to a suspension of 50% NaH (3.5 g) in anhydrous THF (100 ml). The suspension was stirred at ambient temperature for 30 min and then a solution of triethylene glycol methyl tosyl ether from above (22.0 g) in THF (100 ml) was added dropwise. The mixture was refluxed under nitrogen overnight, cooled to ambient temperature, quenched with water (500 ml), and extracted with diethyl ether (3×300 ml). The ether extracts were combined, dried (sodium sulfate), and concentrated in vacuo to give nonaethylene glycol benzyl methyl ether as an oil (27 g, 88%), $^1$H-NMR (CDCl$_3$) δ: 7.31 (m, 5, 5 phenyl CH), 4.54 (s, 2, benzyl CH$_2$), 3.62–3.52 (m, 36, 18 CH$_2$O), 3.35 (s, 3, CH$_3$).

A solution of nonaethylene glycol benzyl methyl ether from above (38 g) in methanol (200 ml) was shaken with 10% palladium on activated charcal (Aldrich, 1.0 g) under hydrogen (50 psi) on a Parr apparatus overnight. The catalyst was filtered off (Celite), and the filtrate was concentrated in vacuo to provide nonaethylene glycol monomethyl ether as an oil (23 g, 74%), $^1$H-NMR (CDCl$_3$) δ: 3.67–3.47 (m, 36, 18 OCH$_2$), 3.32 (s, 3, CH$_3$).

Anal. Calcd for C$_{19}$H$_{40}$O$_{10}$: C, 53.26; H, 9.41. Found: C, 53.25; H, 9.41.

(b) (E)-4-(1,3-Bis(cyclohexylmethyl)-1,2,3,6-tetrahydro-2,6-dioxo-9H-purin-8-yl)cinnamic Acid Nonaethylene Glycol Monomethyl Ether Ester A mixture of 4-formylcinnamic acid (Aldrich, 22.0 g), nonaethylene glycol monomethyl ether (from step (a), 6.00 g), and toluene sulfonic acid (Aldrich, 10 g) in dry xylenes (600 ml) was refluxed for 4 h (oilbath) until about 2.0 ml (110 mmol) of water had collected in a Dean Stark trap. The reaction mixture was then concentrated to about 100 ml, cooled to ambient temperature, and passed through a silica gel column. 4-Formylcinnamic acid nonaethylene glycol methyl ether ester eluted with chloroform:acetone (60:40) as an oil (72 g, 97%), $^1$H-NMR (CDCl$_3$) d: 10.01 (s,1, CHO), 7.89 (d, J=8.1 Hz, 2, 2 phenyl CH), 7.71 (d, J=16.1 Hz, 1, CH=), 7.66 (d, J=8.0 Hz, 2, 2 phenyl CH), 6.57 (d, J=16.1 Hz, 1, CH=), 4.37 (m, 2, CO$_2$CH$_2$), 3.77 (m, 2, CH$_2$O), 3.67–3.52 (m, 32, 16 CH$_2$O), 3.35 (s, 3, CH$_3$).

The title compound was prepared from 1,3-bis(cyclohexylmethyl)-5,6-diaminouracil by the method of J. Perutmattam, Syn. Commun. 1989, 19:3367–3370. In the manner of step (d) of example 9, 1,3-bis(cyclohexylmethyl)-5,6-diaminouracil (from step (d) example 1, 10.4 g) was condensed with 4-formylcinnamic acid nonaethylene glycol monomethyl ether from above (18.0 g) to provide the title compound as a light yellow solid (20.0 g, 74%), m.p. 143–145° C.; $^1$H-NMR (DMSO-d$_6$) δ: 8.28 (d, J=8.3 Hz, 2, 2 phenyl CH), 7.74 (d, J=16.2 Hz, 1, CH=), 7.67 (d, J=8.4 Hz, 2, 2 phenyl CH), 6.55 (d, J=15.9 Hz, 1, CH=), 4.40 (m, 2, CO$_2$CH$_2$), 4.08 (d, J=6.9 Hz, 2, CH$_2$N), 4.00 (d, J=7.3 Hz, 2, CH$_2$N), 3.80 (m, 2, CH$_2$O), 3.72–3.52 (m, 32, 16 CH$_2$O), 3.35 (s, 3, CH$_3$), 2.05–1.03 (m, 22, 2 cyclohexyl).

Anal. Calcd for C$_{47}$H$_{72}$N$_4$O$_{13}$: C, 62.65; H, 8.05; N, 6.32. Found: C, 62.40; H, 7.92; N, 6.42.

Example 11

(E)-4-(1,3-Bis(cyclohexylmethyl)-1,2,3,6-tetrahydro-2,6-dioxo-9H-purin-8-yl)cinnamic Acid Polyethylene Glycol (n=11.7) Methyl Ether Ester A slurry of (E)-4-[1,3 bis(cyclohexylmethyl)-1,2,3,6-tetrahydro-2,6-dioxo-9H-purin-8-yl]cinnamic acid (from step (d) example 1, 5.50 g) in poly(ethyleneglycol) monomethyl ether (Aldrich, average molecular weight 550, 365 g, dried by evaporation of toluene prior to use) containing sulfuric acid (0.57 g) was stirred at 1 Torr for 15 min. The yellow reaction mixture was then stirred at 190° C. (oilbath) and 1 Torr for 3 h, during which time the solids dissolved, leaving a brown solution. After cooling to ambient temperature, the dark solution was poured onto water (150 ml). The aqueous mixture was stirred for 1.5 h before being extracted with dichloroethane (3×120 ml). The combined extracts were then washed with water (150 ml) and the pH of the aqueous layer was adjusted to a value of 6.5 by the addition of concentrated ammonium hydroxide. After drying (sodium sulfate), the extracts were concentrated and the resulting oil was chromatographed on C-18 reverse phase silica gel (EM Separations LiChroprep RP-18). The column was eluted with a gradient from 30% water-methanol to neat methanol; crude product eluted in neat methanol. This orange waxy solid was further chromatographed on silica gel. The title compound eluted in 1–5% methanol in chloroform as a yellow waxy solid, which was then dissolved in chloroform and precipitated through the addition of hexanes to provide title compound as a light-yellow waxy solid (6.34 g, 56 %), m.p. 140–143° C.; $^1$H-NMR (DMSO-d$_6$) δ: 8.15 (d, J=8.5 Hz, 2, 2 phenyl CH), 7.88 (d, J=8.5 Hz, 2, 2 phenyl CH), 7.70 (d, J=16.0 Hz, 1, CH=), 6.77 (d, J=16.1 Hz, 1, CH=), 4.28 (m, 2, CO$_2$CH$_2$), 3.92 (d, J=7.0 Hz, 2, CH$_2$N), 3.78 (d, J=17.2 Hz, 2, CH$_2$N), 3.70 (m, 2, CH$_2$O), 3.6–3.35 (m, ca 42, ca 10.5 CH$_2$CH$_2$O), 3.23 (s, 3, CH$_3$), 2.0–1.5 and 1.3–0.9 (both br m, 22 total, 2 cyclohexyl).

Anal. Calcd for C$_{29}$H$_{36}$N$_4$O$_4$ (C$_2$H$_4$O)$_{11.6}$·0.4 H$_2$O: C, 61.30; H, 8.20; N, 5.48. Found: C, 61.24; H, 8.26; N, 5.54.

Example 12

(E)-4-(1,3-Bis(cyclohexylmethyl)-1,2,3,6-tetrahydro-2,6-dioxo-9H-purin-8-yl)cinnamic Acid Hexaethylene Glycol Ester (a) 4-Formylcinnamic Acid Hexaethylene Glycol Ester (E)-Methyl 4-(dimethoxymethyl)cinnamate (from step (b) example 9, 16.1 g, 68.1 mmol), and titanium isopropoxide (Aldrich, 6.34 g) were stirred in an excess of crude hexaethylene glycol mono(tetrahydropyranyl) ether (J. W. Cornforth, E. D. Morgan, K. T. Potts, R. J. W. Rees, Tetrahedron 1973, 29:1659–1667, 52.76 g) at ambient temperature for 3 d. The solution was then stirred under vacuum (2 Torr) at 120° C. for 4 h. After the solution had cooled to 32° C., hydrochloric acid (1 N, 80 ml, 80 mmol) was added. The resulting aqueous solution was stirred for 1.5 h at 32–40° C. before being diluted with water (10 ml). The solution was stirred for an additional 30 min before another 10 ml portion of water was added. After 2.5 h, the solution was cooled to ambient temperature and extracted with toluene (3×100 ml). The toluene extracts were combined, dried (sodium sulfate), and concentrated to an oil (33.81 g), which was chromatographed on silica gel. The title compound eluted in 10% methanol in ethyl acetate, and was dried by evaporation of ethanol to provide title compound as a waxy yellow solid (8.80 g, 29%) $^1$H-NMR (DMSO-d$_6$) δ: 10.06 (s, 1, CHO), 7.98 (m, 4, 4 phenyl CH), 7.77 (d, J=16.0 Hz, 1, CH=), 6.88 (d, J=16.0 Hz, 1, CH=), 4.60 (m, 1, OH), 4.31 (m, 2, CO$_2$CH$_2$), 3.71 (m, 2, CH$_2$O), 3.51 (m, 20, 10 CH$_2$O).

Anal. Calcd for C$_{22}$H$_{32}$O$_9$·0.35 H$_2$O·0.25 C$_2$H$_6$O: C, 58.97; H, 7.52; Found: C, 58.43; H, 7.40.

(b) (E)-4-(1,3-Bis(cyclohexylmethyl)-1,2,3,6-tetrahydro-2,6-dioxo-9H-purin-8-yl)cinnamic Acid Hexaethylene Glycol Ester The title compound was prepared from 1,3-bis(cyclohexylmethyl)-5,6-diaminouracil by the method of J. Perutmattam, Syn. Commun. 1989, 19:3367–3370. In the manner of step (d) of Example 9, 1,3-bis(cyclohexylmethyl)-5,6-diaminouracil (from step (d) example 1, 7.68 g) was condensed with 4-formylcinnamic acid hexaethylene glycol ester (from step (a), 10.52 g) to provide the title compound as a light yellow solid (8.0 g, 45%), m.p. 165–168° C.; $^1$H-NMR (DMSO-d$_6$) δ: 8.17 (d, J=8.4 Hz, 2, 2 phenyl CH), 7.90 (d, J=8.4 Hz, 2, 2 phenyl CH), 7.78 (d, J=16.0 Hz, 1, CH=), 6.80 (d, J=16.0 Hz, 1, CH=), 4.60 (m, 1, OH), 4.30 (m, 2, CO$_2$CH$_2$), 3.93 (d, J=6.9 Hz, 2, CH$_2$N), 3.80 (d, J=7.2 Hz, 2, CH$_2$N), 3.71 (m, 2, CH$_2$O), 3.65–3.40 (m, 20, 10 CH$_2$O), 2.1–1.5 and 1.6–0.9 (both br m, 22 total, 2 cyclohexyl).

Anal. Calcd for $C_{40}H_{58}N_4O_{10} \cdot 0.9\ H_2O$: C, 62.30; H, 7.82; N, 7.27 Found: C, 62.33; H, 7.80; N, 7.26.

Example 13

(E)-4-(1,3-bis(cyclohexylmethyl)-1,2,3,6-tetrahydro-2,6-dioxo-9H-purin-8-yl)cinnamic acid polyethylene glycol (n=23.9) methyl ether ester (a) (E)-1,3-Bis(cyclohexylmethyl)-8-(4-(2-(1H-imidazol-1-ylcarbonyl)vinyl)phenyl)-9H-purin-2,6(1H,3H)-dione A slurry of (E)-4-[1,3 bis(cyclohexylmethyl)-1,2,3,6-tetrahydro-2,6-dioxo-9H-purin-8-yl]cinnamic acid (from step (d) example 1, 2.97 g) in anhydrous N,N-dimethylformamide (50 ml) was heated briefly to near reflux under nitrogen. N,N'-Carbonyldiimidazole (Lancaster Synthesis, 1.17 g) was then added to the pale yellow slurry, which thinned and turned orange as a gas evolved. Within minutes the slurry turned a bright yellow and thickened as a yellow solid formed. The mixture was stirred for 18 h, diluted with dichloromethane (30 ml), and filtered. The bright yellow filter plug was washed with dichloromethane (30 ml), and partially air-dried. The wet solid was then dried at 0.1 Torr and 40° C. to provide (E)-1,3-bis(cyclohexylmethyl)-8-(4-(2-(1H-imidazol-1-ylcarbonyl)vinyl)phenyl)-9H-purin-2,6(1H,3H)-dione as a yellow powder (3.25 g, 96%), m.p. 310° C. (dec); $^1$H-NMR (DMSO-$d_6$) δ: 8.74 (s, 1, imidazole CH), 8.20 (d, J=8.9 Hz, 2, 2 phenyl CH), 8.06 (d, J=7.7 Hz, 2, 2 phenyl CH), 8.03 (d, J=14.8 Hz, 1, CH=), 7.93 (s, 1, imidazole CH), 7.72 (d, J=15.7 Hz, 1, CH=), 7.14 (s, 1, imidazole CH), 3.92 (d, J=7.0 Hz, 2, $CH_2N$), 3.77 (d, J=7.4 Hz, 2, $CH_2N$), 2.00–1.50 and 1.25–0.90 (both br m, 22 total, 2 cyclohexyl).

Anal. Calcd for $C_{31}H_{36}N_6O_3 \cdot 0.35\ C_3H_7NO$: C, 67.98; H, 6.84; N, 15.71. Found: C, 67.93; H, 6.67; N, 15.92.

(b) (E)-4-(1,3-Bis(cyclohexylmethyl)-1,2,3,6-tetrahydro-2,6-dioxo-9H-purin-8-yl)cinnamic Acid Polyethylene Glycol (n=23.9) Methyl Ether Ester A slurry of (E)-1,3-bis(cyclohexylmethyl)-8-(4-(2-(1H-imidazol-1-ylcarbonyl)vinyl)phenyl)-9H-purin-2,6(1H,3H)-dione (from step (a), 2.25 g) in anhydrous N,N-dimethyl formamide (50 ml) was warmed to 60° C. (oil bath) under nitrogen. Poly(ethyleneglycol) monomethyl ether (Shearwater Polymers, average molecular weight 1100, 4.80 g, dried by evaporation of toluene prior to use) was added to the bright yellow slurry, followed by 1,8-diazabicyclo[5.4.0]undec-7-ene (Aldrich, 658 ml). Addition of the base produced a deep red reaction mixture and caused almost complete dissolution of the acyl imidazole. The red mixture was stirred at 60° C. for 2.5 d, during which time all solids dissolved. The pH of the light red solution was then adjusted to a value of 5 by the addition of sulfuric acid. Volatiles were removed from the resulting light yellow solution at 0.24 Torr and 47° C. to provide a yellow oil (11.37 g), which was chromatographed on C-18 reverse phase silica gel (EM Separations LiChroprep RP-18). The column was eluted with a gradient from 40% water-methanol to neat methanol; crude product eluted in neat methanol to afford a yellow solid (10.25 g), which was further chromatographed on silica gel. The title compound eluted with 4–10% methanol in dichloromethane as a pale yellow glass (5.73 g, 92%), which was triturated with hexanes to provide a waxy yellow solid, m.p. 97–98° C.; $^1$H-NMR (DMSO-$d_6$) δ: 8.18 (d, J=8.2 Hz, 2, 2 phenyl CH), 7.91 ( d, J=8.6 Hz, 2, 2 phenyl CH), 7.72 (d, J=15.8 Hz, 1, CH=), 6.79 (d, J=15.9 Hz, 1, CH=), 4.30 (m, 2, $CO_2CH_2$), 3.94 (d, J=7.0 Hz, 2, $CH_2N$), 3.80 (d, J=7.8 Hz, 2, $CH_2N$), 3.70 (m, 2, $CH_2O$), 3.57–3.41 (m, ca 88, ca 44 $CH_2O$), 3.25 (s, 3, $CH_3$), 2.0–1.5 and 1.3–0.9 (both br m, 22 total, 2 cyclohexyl).

Anal. Calcd for $C_{29}H_{36}N_4O_4\ (C_2H_4O)_{23.4} \cdot 0.30\ H_2O$: C, 59.02; H, 8.53; N, 3.58. Found: C, 59.05; H, 8.57; N, 3.62.

Example 14

(E)-4-(1,3-Bis(cyclohexylmethyl)-1,2,3,6-tetrahydro-2,6-dioxo-9H-purin-8-yl)cinnamic Acid Polyethylene Glycol (n=41.5) Methyl Ether Ester In the manner of example 13, (E)-1,3-bis(cyclohexylmethyl)-8-(4-(2-(1H-imidazol-1-ylcarbonyl)vinyl)phenyl)-9H-purin-2,6(1H,3H)-dione (from step (a) example 13, 2.16 g) was coupled to poly(ethyleneglycol) monomethyl ether (Aldrich, average molecular weight 2000, 9.60 g) to provide the title compound as a yellow powder (6.80 g, 76%), m.p. 56–64° C.; $^1$H-NMR (DMSO-$d_6$) δ: 8.18 (d, J=8.2 Hz, 2, 2 phenyl CH), 7.91 (d, J=8.2 Hz, 2, 2 phenyl CH), 7.72 (d, J=16.0 Hz, 1, CH=), 6.80 (d, J=16.1 Hz, 1, CH=), 4.30 (m, 2, $CO_2CH_2$), 3.70–4.00 (m, 6, 2 $CH_2N$ and $CH_2O$), 3.70–3.40 (m, ca 160, ca 80 $CH_2O$), 3.25 (s, 3, $CH_3$), 2.0–1.5 and 1.3–0.9 (both br m, 22 total, 2 cyclohexyl).

Anal. Calcd for $C_{29}H_{36}N_4O_4\ (C_2H_4O)_{41.5}$: C, 57.67; H, 8.73; N, 2.40. Found: C, 57.51; H, 8.51; N, 2.31.

Example 15

(E)-4-(1,3-Bis(cyclohexylmethyl)-1,2,3,6-tetrahydro-2,6-dioxo-9H-purin-8-yl)cinnamic Acid Polyethylene Glycol (n=15) Methyl Ether Ester In the manner of example 13, (E)-1,3-bis(cyclohexylmethyl)-8-(4-(2-(1H-imidazol-1-ylcarbonyl)vinyl)phenyl)-9H-purin-2,6(1H,3H)-dione (from step (a) example 13, 2.16 g, 3.84 mmol) was coupled to poly(ethyleneglycol) monomethyl ether (Aldrich, average molecular weight 750, 3.30 g, 4.40 mmol) to provide the title compound as a yellow waxy solid (3.30 g, 74%), m.p. 124–125° C.; $^1$H-NMR (DMSO-$d_6$) δ: 8.18 (d, J=8.2 Hz, 2, 2 phenyl CH), 7.91 (d, J=8.4 Hz, 2, 2 phenyl CH), 7.72 (d, J=16.0 Hz, 1, CH=), 6.80 (d, J=16.0 Hz, 1, CH=), 4.31 (m, 2, $CO_2CH_2$), 3.94 (m, 2, $CH_2N$), 3.80 (m, 2, $CH_2N$), 3.70 (m, 2, $CH_2O$), 3.6–3.4 (m, ca 58, ca 29 $CH_2O$), 3.25 (s, 3, $CH_3$), 1.8–1.5 and 1.3–0.9 (both br m, 22 total, 2 cyclohexyl).

Anal. Calcd for $C_{29}H_{36}N_4O_4\ (C_2H_4O)_{15} \cdot 0.5\ H_2O$: C, 57.67; H, 8.73; N, 2.40. Found: C, 57.51; H, 8.51; N, 2.31.

Example 16

(E)-4-(1,3-Bis(cyclohexylmethyl)-1,2,3,6-tetrahydro-2,6-dioxo-9H-purin-8-yl)cinnamic Acid Polyethylene Glycol (n=32.2) Ester (E)-1,3-Bis(cyclohexylmethyl)-8-(4-(2-(1H-imidazol-1-ylcarbonyl)vinyl)phenyl)-9H-purin-2,6(1H,3H)-dione (from step (a) example 13, 1.69 g) was added to molten poly(ethyleneglycol) (Aldrich, average molecular weight 1500, 90.0 g, 60.0 mmol, dried by evaporation of toluene prior to use) under nitrogen. The yellow slurry was diluted with anhydrous N,N-dimethyl formamide (40 ml), and heated to 60° C. (oilbath). 1,8-Diazabicyclo[5.4.0]undec-7-ene (Aldrich, 494 ml) was then added, producing a deep red reaction mixture and causing almost complete dissolution of the acyl imidazole. The mixture was stirred at 60° C. for 16.5 h, during which time all solids dissolved. The pH of the orange solution was then adjusted to 5 through the addition of sulfuric acid. Volatiles were removed from the resulting yellow solution at 0.7 Torr and 50° C., and the residual orange oil was chromatographed on C-18 reverse phase silica gel (EM Separations LiChroprep RP-18). The column was eluted with a gradient from 40% water-methanol to neat methanol; crude product eluted in neat methanol to give a yellow film (8.50 g), which was further chromatographed on silica gel. The title compound eluted with 6–15% methanol in dichloromethane as a pale yellow glass (5.83 g), which was triturated with hexanes to provide a waxy yellow solid (4.773 g, 83%), m.p. 83–84° C.; $^1$H-NMR (DMSO-$d_6$) δ: 13.92 (s, 1 NH), 8.14 (d, J=8.4 Hz, 2, 2 phenyl CH), 7.87 (d, J=8.5 Hz, 2, 2 phenyl CH), 7.68 (d, J=15.7 Hz, 1, CH═), 6.76 (d, J=16.1 Hz, 1, CH═), 4.56 (t, J=5.5 Hz, 1, OH), 4.26 (m, 2, $CO_2CH_2$), 3.90 (d, J=7.3 Hz, 2, $CH_2N$), 3.76 (d, J=6.9 Hz, 2, $CH_2N$), 3.66 (m, 2, $CH_2O$), 3.6–3.2 (m, ca 120, ca 60 $CH_2O$), 2.0–1.5 and 1.3–0.8 (both br m, 22 total, 2 cyclohexyl).

Anal. Calcd for $C_{28}H_{34}N_4O_4$ $(C_2H_4O)_{32.2}$·0.2 $H_2O$: C, 58.02; H, 8.60; N, 2.93. Found: C, 58.01; H, 8.59; N, 2.92.

Example 17

(E)-4-(1,3-Bis(cyclohexylmethyl)-1,2,3,6-tetrahydro-2,6-dioxo-9H-purin-8-yl)cinnamic Acid Polyethylene Glycol (n=18.9) Ester In the manner of example 16, (E)-1,3-bis(cyclohexylmethyl)-8-(4-(2-(1H-imidazol-1-ylcarbonyl)vinyl)phenyl)-9H-purin-2,6(1H,3H)-dione (from step (a) example 13, 1.69 g) was coupled to poly(ethyleneglycol) (Aldrich, average molecular weight 1000, 60.0 g) to provide the title compound as a yellow waxy solid (2.747 g, 85%), m.p. <40° C.; $^1$H-NMR (DMSO-$d_6$) δ: 13.88 (s, 1, NH), 8.11 (d, J=8.0 Hz, 2, 2 phenyl CH), 7.83 (d, J=8.4 Hz, 2, 2 phenyl CH), 7.66 (d, J=16.1 Hz, 1, CH═), 6.73 (d, J=16.1 Hz, 1, CH═), 4.55 (t, J=5.5 Hz, OH), 4.26 (m, 2, $CO_2CH_2$), 3.87 (d, J=6.9 Hz, 2, $CH_2N$), 3.74 (d, J=7.0 Hz, 2, $CH_2N$), 3.66 (m, 2, $CH_2O$), 3.6–3.3 (m, ca 88, ca 40 $CH_2O$, overlapping $H_2O$), 2.1–1.5 and 1.3–0.9 (both br m, 22 total, 2 cyclohexyl).

Anal. Calcd for $C_{28}H_{34}N_4O_4$ $(C_2H_4O)_{18.9}$·1.2 $H_2O$: C, 58.77; H, 8.39; N, 4.17. Found: C, 58.77; H, 8.28; N, 4.10.

Example 18

(E)-4-(1,3-Bis(cyclohexylmethyl)-1,2,3,6-tetrahydro-2,6-dioxo-9H-purin-8-yl)cinnamic Acid Polyethylene Glycol (n=13) Ester In the manner of example 16, (E)-1,3-bis(cyclohexylmethyl)-8-(4-(2-(1H-imidazol-1-ylcarbonyl)vinyl)phenyl)-9H-purin-2,6(1H,3H)-dione (from step (a) example 13, 5.553 g) was coupled to poly(ethyleneglycol) (Dow, average molecular weight 600, 121.0 g) to provide the title compound as a yellow waxy solid (6.94 g, 64%), m.p. 142–143° C.; $^1$H-NMR (DMSO-$d_6$) δ: 8.18 (d, J=8.4 Hz, 2, 2 phenyl CH), 7.90 (d, J=8.4 Hz, 2, 2 phenyl CH), 7.72 (d, J=16.0 Hz, 1, CH═), 6.79 (d, J=16.0 Hz, 1, CH═), 4.58 (t, J=5.3 Hz, OH), 4.30 (m, 2, $CO_2CH_2$), 3.94 (d, J=7.2 Hz, 2, $CH_2N$), 3.80 (d, J=7.0 Hz, 2, $CH_2N$), 3.70 (m, 2, $CH_2O$), 3.61–3.42 (m, ca 48, ca 24 $CH_2O$), 2.0–1.5 and 1.3–0.9 (both br m, 22 total, 2 cyclohexyl).

Anal. Calcd for $C_{28}H_{34}N_4O_4$ $(C_2H_4O)_{13}$·1 $H_2O$: C, 59.98; H, 8.20; N, 5.18 Found: C, 59.96; H, 8.18; N, 5.13.

Example 19

3-{4-[1,3-Bis(cyclohexylmethyl)-1,2,3,6-tetrahydro-2,6-tetrahydro-2,6-dioxo-9H-purin-8-yl] phenyl}propionic Acid Nonaethylene Glycol Monomethyl Ether Ester A solution of (E)-4-(1,3-Bis(cyclohexylmethyl)-1,2,3,6-tetrahydro-2,6-dioxo-9H-purin-8-yl)cinnamic acid nonaethylene glycol monomethyl ether ester (from step (b) example 10, 200 mg) in isopropanol (50 ml) was stirred under $H_2$ (0.02 Bar) in the presence of 10% palladium on activated charcoal (Aldrich, 40 mg) in a Büchi Pressflow Hydrogenator for 23 h. The catalyst was filtered off (Celite), and volatiles were evaporated under vaccuum. Chloroform (5×10 ml) was evaporated from the oily residue, which, after drying (0.2 mm Hg, 50° C.) afforded the title compound as a waxy yellow solid (165 mg, 83%), m.p. 85–86° C., $^1$H-NMR (DMSO-$d_6$) consistent with structure.

Anal. Calcd for $C_{47}H_{74}N_4O_{13}$: C, 62.51; H, 8.26; N, 6.21. Found: C, 62.39; H, 8.27; N, 6.27.

Example 20

3[-4-[1,3-Bis(cyclohexylmethyl)-1,2,3,6-tetrahydro-2,6-dioxo-9H-purin-8-yl]phenyl}propiolic Acid Nonaethylene Glycol Methyl Ether Ester (a) 3-[4-[1,3-Bis(cyclohexylmethyl)-1,2,3,6-tetrahydro-2,6-dioxo-9H-purin-8-yl]phenyl}-2,3-dibromopropionic Acid Ethyl Ester A solution of 0.64 g (4.0 mmol) bromine in 10 mL chloroform was added to a stirred solution of 1.90 g (3.66 mmol) (E)-4-(1,3-bis(cyclohexylmethyl)-1,2,3,6-tetrahydro-2,6-dioxo-9H-purin-8-yl)cinnamic acid ether ester in 25 mL chloroform. The mixture was stirred at room temperature, then the solvent was evaporated to yield the title compound as a white solid. (2.5 g, 100%) $^1$H-NMR (CDCl$_3$) δ: 8.31 (d, J=8.4 Hz, phenyl CH, 2H), 7.56 (d, J=8.4 Hz, phenyl CH, 2H), 5.40 (d, J=11.7 Hz, CHBr, 1H), 4.83 (d, J=11.7 Hz, CHBr, 1H), 4.38 (q, J=7.3 Hz, $CO_2CH_2$, 2H), 4.08 (d, J=7.2 Hz, $CH_2N$, 2H), 4.03 (d, J=7.3 Hz, $CH_2N$, 2H), 2.04 (m, c-hexyl CH, 1H), 1.89 (m, c-hexyl CH, 1H), 1.5–1.8 (m, c-hexyl $CH_2$, 10 H), 1.39 (t, J=7.3 Hz, terminal-$CH_3$, 3H), 1.0–1.3 (m, c-hexyl $CH_2$, 10 H).

(b) 3-[4-[1,3-Bis(cyclohexylmethyl)-1,2,3,6-tetrahydro-2,6-dioxo-9H-purin-8-yl]phenyl}propiolic Acid 2.8 g (4.1 mmol) 3-[4-[1,3-bis(cyclohexylmethyl)-1,2,3,6-tetrahydro-2,6-dioxo-9H-purin-8-yl]phenyl}-2,3-dibromo-propionic acid ethyl ester (part a of this example) was added to 56 mL of 1M potassium t-butoxide in t-butanol (Aldrich) at room temperature. The mixture was stirred at room temperature for 2.5 hours, then 0.10 mL water was added. The solution was stirred for an additional hour then 1 g charcoal was added in 250 mL water. The mixture was stirred for 30 minutes then filtered. The filtrate was acidified with conc. hydrochloric acid (pH=1), then the resulting suspension was stirred for 15 minutes, filtered then washed with 3×50 mL water. The solid was dried under reduced pressure to give 1.63 g (81%) of title compound; $^1$H-NMR (DMSO-$d_6$)δ: 8.15 (d, J=8.0 Hz, phenyl CH, 2H), 7.73 (d, J=8.0 Hz, phenyl CH, 2H), 3.87 (d, J=6.6 Hz, $CH_2N$, 2H), 3.74 (d, J=6.8 Hz, $CH_2N$, 2H), 1.88 (br s, c-hexyl CH, 1H), 1.4–1.8 (m, c-hexyl CH, $CH_2$, 11H), 0.8–1.2 (m, c-hexyl $CH_2$, 10 H); MS (ES$^-$): 487 (M–1), 443 (M–1–$CO_2$).

(c) 3-[4-[1,3-Bis(cyclohexylmethyl)-1,2,3,6-tetrahydro-2,6-dioxo-9H-purin-8-yl]phenyl}propiolic Acid Nonaethylene Glycol Methyl Ether Ester A solution of 324 mg (2.0) mmol 1,1'-carbonyldiimidazole in 10 mL acetonitrile was added to a stirred solution of 650 mg (1.33 mmol) 3-[4-[1,3-bis(cyclohexylmethyl)-1,2,3,6-tetrahydro-2,6-dioxo-9H-purin-8-yl]phenyl}propiolic acid in 40 mL anhydrous tetrahydrofuran. The mixture was stirred for 4 hours, then 40 mL acetonitrile was added, and the suspension was stirred for an additional 30 minutes and filtered. The solid was washed with 2×10 mL acetonitrile and dried overnight under reduced pressure, then mixed with 10 mL of anhydrous dimethyl formamide. Nonaethylene glycol monomethyl ether (857 mg) was added to the suspension and the mixture was stirred under nitrogen. 1,8-diazabicyclo[5.4.0]undec-7-ene (300 μL) was added dropwise and the red solution was stirred at room temperature for an hour, then at 40° C. for an additional hour. The solution was cooled to 20° C., 100 mL of methylene chloride added, and the pH adjusted to 5 with 1 M potassium hydrogensulfate. Phases were separated and the aqueous phase was washed with 2×20 mL methylene chloride. The combined organic phases were dried with anhydrous magnesium sulfate, then filtered. The filtrate was concentrated under reduced pressure, and the residue was purified by silica gel chromatography using ethyl acetate/ethanol (9:1) as eluent, to obtain 105 mg (9%) title compound; $^1$H-NMR (CDCl$_3$) δ: 8.27 (d, J=8.3 Hz, phenyl CH, 2H), 7.71 (d, J=8.3 Hz, phenyl CH, 2H), 4.41 (t, J=4.6 Hz, CO$_2$CH$_2$, 2H), 4.06 (d, J=7.3 Hz, CH$_2$N, 2H), 3.97 (d, J=7.2 Hz, CH$_2$N, 2H), 3.78 (t, J=4.8 Hz, CH$_2$O, 2H), 3.6–3.7 (m, 15 CH$_2$, 30 H), 3.52 (m, CH$_2$O, 2H), 3.34 (s, OCH$_3$, 3H), 2.04 (m, c-hexyl CH, 1H), 1.85 (m, c-hexyl CH, 1H), 1.6–1.8 (m, c-hexyl CH, CH$_2$, 10H), 1.0–1.2 (m, c-hexyl CH$_2$, 10 H). MS (FAB$^+$): 899 (M+1), 921 (M+Na).

Example 21

(E)-3-[1,3-Bis(cyclohexylmethyl)-1,2,3,6-tetrahydro-2,6-dioxo-9H-purin-8-yl]cinnamic Acid Nonaethylene Glycol Methyl Ether Ester (a) (E)-3-[(1,3-Bis(cyclohexylmethyl)-1,2,3,6-tetrahydro-2,6-dioxo-9H-purin-8-yl]cinnamic acid As in part (d) of Example, 1, 6-amino 1,3-bis(cyclohexylmethyl)-5-nitrosouracil (from step (c) example 1, 2.79 g, 8.00 mmol) was reduced to 1,3-bis(cyclohexylmethyl)-5,6-diaminouracil, and condensed with 3-Formylcinnamic acid (T. Higa, A. J. Krubsack, J. Org. Chem. 1975, 40: 3037–3045, 1.424 g) to give (E)-3-[1,3-bis(cyclohexylmethyl)-1,2,3,6-tetrahydro-2,6-dioxo-9H-purin-8-yl]cinnamic acid as an off-white solid (1.947 g, 49%), m.p. >350° C.; $^1$H-NMR (DMSO-d$_6$) consistent with structure.

Anal. Calcd for C$_{28}$H$_{34}$N$_4$O$_4$·0.10 H$_2$O: C, 68.30; H, 7.00; N, 11.38. Found: C, 68.33; H, 6.93; N, 11.34.

(b) (E)-3-[1,3-Bis(cyclohexylmethyl)-1,2,3,6-tetrahydro-2,6-dioxo-9H-purin-8-yl]cinnamic Acid Nonaethylene Glycol Methyl Ether Ester A slurry of (E)-3-[1,3-bis(cyclohexylmethyl)-1,2,3,6-tetrahydro-2,6-dioxo-9H-purin-8-yl]cinnamic acid (from step (a), 0.50 g) in anhydrous N,N-dimethylformamide (10 mL) was heated briefly to near reflux under nitrogen. N,N'-carbonyldiimidazole (Aldrich, 0.202 g, 1.22 mmol) was then added to the pale yellow slurry, which thinned and turned orange as a gas evolved. Within minutes the slurry turned a bright yellow and thickened as a yellow solid formed. The mixture was stirred for 18 h, diluted with dichloromethane (30 mL), and filtered. The bright yellow solid was washed with dichloromethane (30 mL), and dried at 40° C. to provide (E)-1,3-bis(cyclohexylmethyl)-8-(3-(2-(1H-imidazol-1-ylcarbonyl)vinyl)phenyl)-9H-purin-2,6(1H,3H)-dione as a yellow powder (0.403 g). To a mixture of this compound (0.40 g, 0.74 mmol) and nonaethylene glycol monomethyl ether, (part (a) of example 10, 0.350 g) in N,N-dimethyl formamide (10 ml) was added 1,8-diazabicyclo[5.4.0]undec-7-ene (Aldrich, 0.112 g). The resulting solution was stirred at 55° C. for 20 h. The solution was cooled to room temperature and adjusted to pH 7 by addition of 1N HCl. Chloroform (50 mL) was added and the solution was washed with water (2×20 mL). The combined organic layers were washed with brine, dried (magnesium sulfate) and concentrated under reduced pressure. The residual waxy solid was chromatrographed on silica gel eluted with 10% methanol/chloroform to give (E)-3-[1,3-bis(cyclohexylmethyl)-1,2,3,6-tetrahydro-2,6-dioxo-9H-purin-8-yl]cinnamic acid nonaethylene glycol methyl ether ester as a white waxy solid (0.421 g, 63%); $^1$H-NMR (DMSO-d$_6$)δ: 8.53 (s, 1, aryl CH), 8.13 (d, J=7.7, 1, aryl CH), and 7.80 (d, J=8.5, 1, aryl CH), 7.71 (d, J=16, 1, CH=) 7.58, (m, 1, aryl CH), 6.78, (d, J=15.9, 1, CH=) 4.28 (m,2, CH$_2$O), 3.91, (d, J=7.2, 2,CH$_2$N), 3.77 (d, J=7.2, CH$_2$N), 3.68 (m, 2, CH$_2$O), 3.70–3.40 (m, 32, 16 CH$_2$), 3.21 (s, 3, CH$_3$), 2.1–1.6 and 1.4–1.0 (m, 22, cyclohexyl CH$_2$ and CH).

Anal. Calcd. For C$_{47}$H$_{72}$N$_4$O$_{13}$: C, 62.65; H, 8.05; N, 6.22. Found: C, 62.57; H, 7.83; N, 6.50

Example 22

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide (a) 2, 5, 8, 11, 14, 17, 20, 23, 26-nonaoxo-octacosyl-28-amine Sodium hydride (8.6 g, 344 mmol as 95%) was added to a solution of hexaethylene glycol (Aldrich, 100 g) in anhydrous tetrahydrofuran (1000 mL) at 15° C. The resulting mixture was stirred while coming to ambient temperature over 1 h. Benzyl bromide (Aldrich, 59.9 g) was added dropwise over 1 h and the resulting mixture stirred at ambient temperature for 16 h. The cooled mixture was diluted with water (200 mL) and extracted with diethyl ether (3×350 mL). The combined diethyl ether extracts were washed with water (2×100 mL). The combined aqueous layers were saturated with sodium chloride and extracted with methylene chloride (4×400 mL). The combined methylene chloride layers were washed with saturated sodium chloride (200 mL) and dried (magnesium sulfate). Removal of the volatiles under reduced pressure left hexaethylene glycol monobenzyl ether (80.5 g, 64%); $^1$H-NMR identical with that described in part (a) of Example 10. A solution of hexaethylene glycol monobenzyl ether (80.0 g) in anhydrous THF (750 mL) was added to a suspension of sodium hydride (95%, 5.4 g) in tetrahydrofuran. The resulting mixture was stirred at ambient temperature for 30 min, and then a solution of triethylene glycol methyl tosyl ether (prepared as described in part (a) of Example 1, 68.4 g) in THF (100 mL) was added dropwise. The mixture was refluxed under nitrogen overnight. Additional sodium hydride (2.5 g) was added and reflux continued an additional 24 h. The mixture was cooled (ice bath), quenched with water (2 L), and extracted with diethyl ether (2×200 mL). The aqueous layer was washed with methylene chloride (2×250 mL). The combined organic layers were dried (magnesium sulfate) and concentrated to a brown oil which was filtered through a silica gel pad washed with methylene chloride. Methylene chloride was evaporated to leave nonaethylene glycol benzyl methyl ether as an oil (63.1 g, 57%), $^1$H-NMR (DMSO-d$_6$) δ: 7.23 (m, 5, 5 phenyl CH), 4.38 (s, 2, benzyl CH$_2$), 3.50–3.30 (m, 36, 18 CH$_2$O), 3.13 (s, 3, CH$_3$).

A solution of nonaethylene glycol benzyl methyl ether (10 g, 19.3 mmol) in ethanol (200 mL) was shaken with 10% palladium on activated charcal (Aldrich, 1.0 g) under hydrogen (50 psi) on a Parr apparatus for 3 h. The catalyst was filtered off (Celite), and the filtrate was concentrated in vacuo and dried by evaporation of toluene to provide nonaethylene glycol monomethyl ether as an oil (8.17 g, 99%), $^1$H-NMR (DMSO-d$_6$) δ: 4.56 (t, 1 OH), 3.60–3.35 (m, 36, 18 OCH$_2$), 3.22 (s, 3, CH$_3$).

To a solution of nonaethylene glycol monomethyl ether (2.0 g. 4.7 mmol) in pyridine (15 mL) at 0° C. was added toluenesulfonyl chloride (1.35 g). After stiring at room temperature overnight, the mixture was cooled to 0° and adjusted to pH 2 by addition of 12N HCl. Water (200 mL) was added and the solution was washed with methylene chloride (3×50 mL). The combined organic layers were washed with brine, dried (magnesium sulfate) and evaporated to provide nonaethylene glycol methyl tosyl ether as a colorless oil (2.7 g); $^1$H-NMR (DMSO-d$_6$)δ: 7.85 and 7.55 (2d, 4, C$_6$H$_4$), 4.18 (m, 2, CH$_2$OTos), 3.7–3.45 (m 34, 17 CH$_2$), 3.2 (s, 3, OCH$_3$) 2.40 (s, 3, CH$_3$).

To a solution of nonaethylene glycol methyl tosyl ether (2.6 g, 4.42 mmol) in N,N-dimethylformamide (10 mL), was added sodium azide (Aldrich, 0.35 g) and sodium iodide (Aldrich, 20 mg). The solution was refluxed 18 h, cooled to room temperature, and diluted with chloroform (50 mL). This solution was washed with water (2×10 mL) and the organic layer dried (magnesium sulfate) and concentrated to a colorless oil (2.25 g). The oil was dissolved in ethanol (100 mL), and stirred with 10% palladium on carbon (Aldrich, 200 mg ) under hydrogen (15 psi) for 48 h on a Buchi hydrogenation apparatus. The catalyst was removed by filtration (Celite) and solvent evaporated to leave 2, 5, 8, 11, 14, 17, 20, 23, 26-nonaoxo-octacosyl-28-amine as a colorless oil (1.59 g, 77%); $^1$H-NMR (DMSO-d$_6$)δ: 3.60–3.40 (m, 36, 18 CH$_2$ and NH$_2$), 3.20 (3, CH$_3$); MS (CI) 428 (100%, M+1).

(b) (E)-4-(1,3-Bis(cyclohexylmethyl)-1,2,3,6-tetrahydro-2,6-dioxo-9H-purin-8-yl)cinnamic Acid Nonaethylene Glycol Methyl Ether Amide To a mixture of E)-1,3-bis(cyclohexylmethyl)-8-(4-(2-(1H-imidazol-1-ylcarbonyl)vinyl)phenyl)-9H-purin-2,6(1H,3H)-dione (part (a) of example 13), (0.5 g, 0.92 mmol) and the 2, 5, 8, 11, 14, 17, 20, 23, 26-nonaoxo-octacosyl-28-amine (part (a) of this example, 0.43 g, 1.0 mmol) in N,N-dimethyl formamide (10 mL) was added 1,8-diazabicyclo[5.4.0]undec-7-ene (Aldrich, 0.168 g). The resulting red solution was stirred at 55° C. for 18 h. Additional amine (0.43 g) was added and heating continued for an additional 20 h. The resulting solution was cooled to room temperature and adjusted to pH 7.0 by addition of 1N hydrochloric acid. Water (25 mL) was added and the solution was washed with ethyl acetate (50 mL). The organic layer was washed with brine, dried (magnesium sulfate) and concentrated under reduced pressure. Chromatography on silica gel eluted the title compound with 10% methanol-chloroform. Evaporation of solvent left title compound as a yellow solid (64 mg, 8%); $^1$H-NMR (DMSO-d$_6$)δ: 8.24 (t, 1, NH), 8.15 (d, J=8.4, 2, 2 aryl CH), 7.69 (d, J=8.3, 2, 2 aryl CH), 7.47 (d, J=15.5, 1, CH=), 6.75 (d, J=15.8, 1, CH=), 3.92 (d, J=7.1, 2, CH$_2$N), 3.78 (d, J=7.2, 2, CH$_2$N), 3.6–3.3 (m, 36, 18 CH$_2$), 3.23 (s, 3, CH$_3$), 2.0–1.5 and 1.25–0.95 (both m, 22, cyclohexyl CH$_2$ and CH).

Anal. Calcd for C$_{47}$H$_{73}$N$_5$O$_{12}$.0.85 H$_2$O: C, 61.67; H, 8.22; N, 7.65. Found: C, 61.66; H, 8.07; N, 7.67.

Example 23

(E)-3-[(1,3-Bis(cyclohexylmethyl)-1,2,3,6-tetrahydro-2,6-dioxo-9H-purin-8-yl]benzoic acid Nonaethylene Glycol Methyl Ether Ester (a) (E)-3-[(1,3-Bis(cyclohexylmethyl)-1,2,3,6-tetrahydro-2,6-dioxo-9H-purin-8-yl]benzoic acid 1,3-Bis(cyclohexylmethyl)-5,6-diaminouracil was prepared as in part (d) of Example 1 by reduction of 1, 6-amino 1,3-bis(cyclohexylmethyl)-5-nitrosouracil (2.00 g) and immediately condensed with 3-formylbenzoic acid (Aldrich, 1.424 g) by the method of J. Perumattam (Synthetic Commun. 1989, 19: 3367–3370) to give title compound as an off-white solid (2.27 g, 85%), m.p. >250° C.; $^1$H-NMR (DMSO-d$_6$) consistent with structure.

Anal. Calcd for C$_{26}$H$_{32}$N$_4$O$_4$: C, 67.22; H, 6.94; N, 12.06. Found: C, 67.10; H, 6.97; N, 12.04.

(b) (E)-3-[(1,3-Bis(cyclohexylmethyl)-1,2,3,6-tetrahydro-2,6-dioxo-9H-purin-8-yl]benzoic acid Nonaethylene Glycol Methyl Ether Ester A slurry of (E)-3-[(1,3-bis(cyclohexylmethyl)-1,2,3,6-tetrahydro-2,6-dioxo-9H-purin-8-yl]benzoic acid (from part (a) of this example, 0.500 g) in anhydrous N,N-dimethylformamide (10 mL) was heated briefly to near reflux under nitrogen. N,N'-Carbonyldiimidazole (Aldrich, 0.213 g) was added to the pale yellow slurry, which thinned and turned orange as a gas evolved. Within minutes the slurry turned bright yellow and yellow solid precipitated. The mixture was stirred for 18 h, diluted with dichloromethane (30 mL), and filtered. The solid was washed with dichloromethane (30 mL) and dried at 40° C. to provide (E)-1,3-bis(cyclohexylmethyl)-8-[3-(2-(1H-imidazol-1-ylcarbonyl)vinyl)phenyl]-9H-purin-2,6(1H,3H)-dione as a yellow powder (0.46 g). A mixture of this solid (0.45 g), nonaethylene glycol monomethyl ether, (from part (a) of example 10, 0.393 g) and anhydrous potassium carbonate (0.242 g) in acetonitrile (10 mL) was stirred at reflux for 20 h. Chloroform (50 mL) was added and the solution was washed with 1N HCl, (20 mL). The organic layer was washed with brine, dried (magnesium sulfate), and chromatographed on silica gel. Elution with 10% methanol-chloroform evaporation of solvents gave (E)-3-[1,3-bis(cyclohexylmethyl)-1,2,3,6-tetrahydro-2,6-dioxo-9H-purin-8-yl]benzoic acid nonaethylene glycol methyl ether ester as a waxy white solid (0.262 g, 38%); $^1$H-NMR (DMSO-d$_6$)δ: 8.79 (s) and 8.43 (d, J=7.9), 8.11 (d, J=8.0), and 7.57 (m, each 1,C$_6$H$_4$), 4.50 (m, 2, CH$_2$O), 3.99 (d, J=7.1, 2, CH$_2$N), 3.83 (m, 4, CH$_2$N and CH$_2$O), 3.70–3.40 (m, 32, 16 CH$_2$), 3.28 (s, 3, CH$_3$), 2.1–1.6 and 1.4–1.0 (both m, 22, cyclohexyl CH$_2$ and CH).

Anal. Calcd. For C$_{45}$H$_{70}$N$_4$O$_{13}$.0.52 H$_2$O: C, 61.05; H, 8.10; N, 6.33. Found: C, 61.05; H, 8.09; N, 6.25.

Example 24

(E)-4-[(1,3-Bis(cyclohexylmethyl)-1,2,3,6-tetrahydro-2,6-dioxo-9H-purin-8-yl]benzoic acid Nonaethylene Glycol Methyl Ether Ester (a) (E)-4-[(1,3-Bis(cyclohexylmethyl)-1,2,3,6-tetrahydro-2,6-dioxo-9H-purin-8-yl]benzoic acid 1,3-Bis(cyclohexylmethyl)-5,6-diaminouracil was prepared as in part (d) of Example 1 by reduction of 1, 6-amino 1,3-bis(cyclohexylmethyl)-5-nitrosouracil (1.00 g) and immediately condensed with 4-formylbenzoic acid (Aldrich, 1.424 g) by the method of J. Perumattam (Synthetic Commun. 1989, 19: 3367–3370) to give title compound as an off-white solid an off-white solid (720 mg, 54%), m.p. >300° C.; $^1$H-NMR (DMSO-d$_6$) consistent with structure.

Anal. Calcd for $C_{26}H_{32}N_4O_4$: C, 67.23; H, 6.94; N, 12.06. Found: C, 67.29; H, 6.98; N, 12.02.

(b) (E)-4-[(1,3-Bis(cyclohexylmethyl)-1,2,3,6-tetrahydro-2,6-dioxo-9H-purin-8-yl]benzoic acid Nonaethylene Glycol Methyl Ether Ester A slurry of (E)-4-[(1,3-bis(cyclohexylmethyl)-1,2,3,6-tetrahydro-2,6-dioxo-9H-purin-8-yl]benzoic acid (from part (a) of this example, 0.50 g) in anhydrous N,N-dimethylformamide (10 mL) was heated briefly to near reflux under nitrogen. N,N'-Carbonyldiimidazole (Aldrich, 0.211 g) was then added to the pale yellow slurry, which thinned and turned orange as a gas evolved. Within minutes the slurry turned a bright yellow and thickened as a yellow solid formed. The mixture was stirred for 18 h, diluted with dichloromethane (30 mL), and filtered. The bright yellow solid was washed with dichloromethane (30 mL), and dried at 40° C. to provide (E)-1,3-bis(cyclohexylmethyl)-8-[3-(2-(1H-imidazol-1-ylcarbonyl)vinyl)phenyl]-9H-purin-2,6(1H, 3H)-dione as a yellow powder (0.32 g). A mixture of this sample (0.32 g), nonaethylene glycol monomethyl ether (from part (a) of example 10, 0.277 g) and anhydrous potassium carbonate (0.170 g) in acetonitrile (10 mL) was refluxed for 20 h. Chloroform (50 mL) was added and the solution was washed with 1N HCl, (20 mL). The organic layer was washed with brine, dried (magnesium sulfate), and eluted from a silica gel column with 10% methanol-chloroform. Evaporation of solvents left yellow waxy solid which was reprecipitated from ethyl acetate-hexanes. The yellow waxy solid precipitate was filtered and dried to (E)-4-[1,3-bis(cyclohexylmethyl)-1,2,3,6-tetrahydro-2,6-dioxo-9H-purin-8-yl]benzoic acid nonaethylene glycol methyl ether ester (0.355 g, 65%); $^1$H-NMR (DMSO-d$_6$)δ: 8.24 (d, J=8.4, 2, 2 CH), 8.06 (d, I=8.6, 2, 2 CH), 4.40 (m, 2, CH$_2$O), 3.90 (d, J=7.3, 2,CH$_2$N), 3.75 (m, 4, CH$_2$N and CH$_2$O), 3.70–3.40 (m, 32, 16 CH$_2$), 3.19 (s, 3, CH$_3$), 2.1–1.6 and 1.4–1.0 (m, 22, cyclohexyl CH$_2$ and CH).

Anal. Calcd for $C_{45}H_{70}N_4O_{13}$: C, 61.77; H, 8.06; N, 6.40. Found: C, 61.55; H, 7.99; N, 6.52

Example 25

(E)-2-[(1,3-Bis(cyclohexylmethyl)-1,2,3,6-tetrahydro-2,6-dioxo-9H-purin-8-yl]benzoic acid Nonaethylene Glycol Methyl Ether Ester (a) (E)-2-[(1,3-Bis(cyclohexylmethyl)-1,2,3,6-tetrahydro-2,6-dioxo-9H-purin-8-yl]benzoic acid 1,3-Bis(cyclohexylmethyl)-5,6-diaminouracil was prepared as in part (d) of Example 1 by reduction of 1, 6-amino 1,3-bis(cyclohexylmethyl)-5-nitrosouracil (2.00 g) and immediately condensed with 2-formylbenzoic acid (Aldrich, 1.424 g) by the method of J. Perumattam (Synthetic Commun. 1989, 19: 3367–3370) to give title compound as an off-white solid off-white solid (1.22 g, 46%), m.p. 271–274° C.; $^1$H-NMR (DMSO-d$_6$) consistent with structure.

Anal. Calcd for $C_{26}H_{32}N_4O_4$: C, 67.22; H, 6.94; N, 12.06. Found: C, 67.25; H, 6.99; N, 12.11.

(b) (E)-2-[(1,3-Bis(cyclohexylmethyl)-1,2,3,6-tetrahydro-2,6-dioxo-9H-purin-8-yl]benzoic Acid Nonaethylene Glycol Methyl Ether Ester (E)-2-[(1,3-Bis(cyclohexylmethyl)-1,2,3,6-tetrahydro-2,6-dioxo-9H-purin-8-yl]benzoic acid (from part (a) of this example, 0.100 g) was converted by the method of part (b) of Example 24 to (E)-2-[(1,3-bis(cyclohexylmethyl)-1,2,3,6-tetrahydro-2,6-dioxo-9H-purin-8-yl]benzoic acid nonaethylene glycol methyl ether ester (0.082 g, 43%), as a amber oil; $^1$H-NMR (DMSO-d$_6$)δ:. 7.80–7.50 (m, 4, 4 aromatic CH), 4.20 (m, 2, CH$_2$O), 3.80–3.60 (m, 4, 2CH$_2$N), 3.50–3.20 (m, 34, 17 CH$_2$), 3.20, (s,3, CH$_3$), 1.9–1.4 and 1.2–0.8 (m, 22, cyclohexyl).

Anal. Calcd. For $C_{45}H_{70}N_4O_{13}$.0.85 EtOAc.0.64 H$_2$O: C, 60.50; H, 8.18; N, 5.83. Found: C, 60.50; H, 8.19; N, 5.83.

Example 26

(E)-4-(1,3-Bis(cyclohexylmethyl)-1,2,3,6-tetrahydro-6-oxo-2-thioxo-9H-purin-8-yl)cinnamic Acid Nonaethylene Glycol Methyl Ether Ester (E)-4-(1,3-Bis(cyclohexylmethyl)-1,2,3,6-tetrahydro-6-oxo-2-thioxo-9H-purin-8-yl)cinnamic acid (WO 96/04280, 500 mg, 0.99 mmol) was esterified with nonaethylene glycol methyl ether by the method of part (b) of Example 24. Title compound was isolated as a yellow waxy solid (0.145 g, 20%); $^1$H-NMR (DMSO-d$_6$)δ: 8.17 (d, J=8.4, 2, 2 aryl CH), 7.90 (d, J=8.4, 2, 2 aryl CH), 7.69 (d, J=15.9, 1, CH=), 6.77 (d, J=16.1, 1, CH=), 4.53 (d, J=7.0, 2, CH$_2$N), 4.40 (d, J=7.0, 2, CH$_2$N), 4.25 (m, 2, CH$_2$O), 3.70 (m, 2, CH$_2$O), 3.6–3.3 (m, 32, 16 CH$_2$), 3.23 (s, 3, CH$_3$), 2.4–2.0 (2m, 2, 2CH of cyclohexyl), 1.80–1.60 and 1.20–1.0 (both m, 20, cyclohexyl CH$_2$).

Anal. Calcd for $C_{47}H_{73}N_4O_{12}S$.0.89 H$_2$O: C, 60.49; H, 7.97; N, 6.00; S, 3.44. Found: C, 60.49; H, 7.70; N, 6.31; S, 3.55.

Example 27

(E)-4-(1,3-Bis(cyclohexylmethyl)-1,2,3,6-tetrahydro-2,6-dioxo-9H-purin-8-yl)cinnamic Acid Nonaethylene Glycol Methyl Ether Ester To a mixture of (E)-1,3-bis(cyclohexylmethyl)-8-(3-(2-(1H-imidazol-1-ylcarbonyl)vinyl)phenyl)-9H-purin-2,6(1H, 3H)-dione (60.75 g, 0.112 mole) and potassium carbonate (31.0 g, 0.225 mole) in acetonitrile (650 mL) was added nonaethylene glycol monomethyl ether, (part (a) of example 10, 57.8 g, 135 mmol). The mixture was refluxed 18 h, cooled to ambient temperature, and diluted with chloroform (1200 mL). The chloroform solution was washed with 1N hydrochloric acid (800 mL), water (500 mL), and brine (2×200 mL) and dried (magnesium sulfate. Evaporation of chloroform left crude title compound as a yellow waxy solid. This solid was chromatographed twice on silica gel, first using 10% methanol-chloroform and then using 10% methanol-ethyl acetate as eluent, to give the title compound as a yellow waxy solid. Reprecipitation from chloroform-hexanes and drying in vacuo title compound as a yellow waxy solid (64.5 g, 65%); $^1$H-NMR identical to the sample described in Example 10, part (b).

Anal. Calcd for $C_{47}H_{72}N_4O_{13}$: C, 62.65; H, 8.05; N, 6.22. Found: C, 62.33; H, 7.94; N, 6.25

Pharmaceutical Formulation Examples

In the following Examples, the "active ingredient" may be any compound of formula (I) or a pharmaceutically acceptable salt or solvate thereof preferably compound of Examples 2 to 26.

(1) Tablet Formulations (i) Oral

|  | mg/tablet | | |
| --- | --- | --- | --- |
|  | A | B | C |
| Active ingredient | 25 | 25 | 25 |
| Avicel | 13 | — | 7 |
| Lactose | 78 | 47 | — |
| Starch (maize) | — | 9 | — |
| Starch (pregelatinised, NF15) | — | — | 32 |
| Sodium starch glycollate | 5 | — | — |
| Povidone | 3 | 3 | — |
| Magnesium stearate | 1 | 1 | 1 |
|  | 125 | 85 | 65 |

(ii) Sublingual

|  | mg/tablet | |
| --- | --- | --- |
|  | D | E |
| Active ingredient | 25 | 25 |
| Avicel | 10 | — |
| Lactose | — | 36 |
| Mannitol | 51 | 57 |
| Sucrose | — | 3 |
| Acacia | — | 3 |
| Povidone | 3 | — |
| Magnesium stearate | 1 | 1 |
|  | 90 | 125 |

Formulations A to E may be prepared by wet granulation of the first six ingredients with the povidone, followed by addition of the magnesium stearate and compression.

(iii) Buccal

|  | mg/tablet |
| --- | --- |
| Active ingredient | 25 |
| Hydroxypropylmethyl cellulose (HPMC) | 25 |
| Polycarbophil | 39 |
| Magnesium stearate | 1 |
|  | 90 |

The formulation may be prepared by direct compression of the admixed ingredients.

(2) Capsule Formulations (i) Powder

|  | mg/Capsule | |
| --- | --- | --- |
|  | F | G |
| Active ingredient | 25 | 25 |
| Avicel | 45 | — |
| Lactose | 153 | — |
| Starch (1500 NF) | — | 117 |
| Sodium starch glycollate | — | 6 |
| Magnesium stearate | 2 | 2 |
|  | 225 | 150 |

Formulations F and G may be prepared by admixing the ingredients and filling two-part hard gelatin capsules with the resulting mixture.

(ii) Liquid Fill

|  | mg/Capsule | |
| --- | --- | --- |
|  | H | I |
| Active ingredient | 25 | 25 |
| Macrogol 4000 BP | 200 | — |
| Lecithin | — | 100 |
| Arachis oil | — | 100 |
|  | 225 | 225 |

Formulation H may be prepared by melting the Macrogol 4000 BP, dispersing the active ingredient in the melt and filling two-part hard gelatin capsules therewith. Formulation I may be prepared by dispersing the active ingredient in the lecithin and arachis oil and filling soft, elastic gelatin capsules with the dispersion.

(iii) Controlled Release

|  | mg/tablet |
| --- | --- |
| Active ingredient | 25 |
| Avicel | 123 |
| Lactose | 62 |
| Triethylcitrate | 3 |
| Ethyl cellulose | 12 |
|  | 225 |

The formulation may be prepared by mixing and extruding the first four ingredients and spheronising and drying the extrudate. The dried pellets are coated with ethyl cellulose as a release controlling membrane and filled into two-part, hard gelatin capsules.

(3) Intravenous Injection Formulation (i)

|  | % by weight |
| --- | --- |
| Active ingredients | 2% |
| Sodium hydroxide | q.s to pH 7 |
| Water for Injections | to 100% |

The active ingredient is taken up in the citrate buffer and sufficient hydrochloric acid added to affect solution and adjust the pH to 7. The resulting solution is made up to volume and filtered through a micropore filter into sterile glass vials which are sealed and oversealed.

Example G

Powder Capsules for Inhalation

| | |
|---|---|
| Active Ingredient (0.5–7.0 μm powder) | 1.0 mg |
| Lactose (30–90 μm powder) | 49.0 mg |

The powders were mixed until homogeneous and filled into suitably sized hard gelatin capsules (50 mg per capsule).

Example H

Inhalation Aerosol

| | |
|---|---|
| Active Ingredient (0.5–7.0 μm powder) | 50.0 mg |
| Sorbitan Trioleate | 100.00 mg |
| Saccharin Sodium (0.5–7.0 μm powder) | 5.0 mg |
| Methanol | 2.0 mg |
| Trichlorofluoromethane | 4.2 g |
| Dichlorodifluoromethane | to 10.0 ml |

The sorbitan trioleate and methanol were dissolved in the trichloro-fluoromethane. The saccharin sodium and active ingredient were dispersed in the mixture which was then transferred to a suitable aerosol canister and the dichlorofluoromethane injected through the valve system. This composition provides 0.5 mg of active ingredient in each 100 μl dose.

Biological Activity

I) Carrageenan Pleurisy Assay

The antiinflammatory activity of compounds of the invention was determined by the procedure of Vinegar, R, et al., Proc. Soc. Exp. Biol. Med., 1981, 168, 24–32, using male Lewis rats of 150±±}20 grams. The carrageenan dose was 0.075 mg/rat. Pleural exudate was harvested four hours after injection of carrageenan. Acute antiinflammatory activity was determined by inhibition of pleural edema and inflammatory cells (neutrophils) from a negative (vehicle) control group.

2) Acetic Acid Colitis Assay

Anti-inflammatory activity of compounds of the invention was determined in the Acetic Acid Colitis rat model using the procedure of Fretland, D., et al., 1990, 255:572–576 in male Lewis rats 275+25 grams. Compounds were administered either orally or rectally 24, 16 and 4 hours prior to the 40 second instillation of 3% acetic acid solution in the proximal 6 cm of the colon under light anesthesia. The colon was immediately washed with 5 cc of saline. 24 hours later the rats were sacrificed and 6 cm of the proximal colon was excised weighed for edema. Neutrophil inflammation was determined by measuring MPO levels in the scraped colonic mucosa from these rats. Anti-inflammatory activity was quantitated by inhibition of edema formation and mucosal MPO levels compared to the negative control group (vehicle).

Results

| COMPOUND | PEG | n (or avg.) | CARRAGEENAN PLEURISY (4 hr) LOCAL $ED_{50}$ (MG/RAT) | | ACETIC ACID COLITIS (24 hr) ACTIVE DOSE [MG/KG] (ROUTE) | |
|---|---|---|---|---|---|---|
| | | | CELLS | EDEMA | MPO | TISSUE WEIGHT |
| Dexamethasone | | | 0.02 | 0.015 | 0.03 (ic) | 0.17 (ic) |
| Example 9 | $CH_3$ | 10 | 0.02 | 0.2 | 5.0 (ic) | 5.0 (ic) |
| Example 10 | $CH_3$ | 9 | 0.5 | 0.5 | 50 (po) | 50 (po) |
| Example 15 | $CH_3$ | 15 or 16 | 0.4 | 0.2 | 50 (po) | inactive (50, po) |
| Example 14 | $CH_3$ | 41.5 | Inactive 0.5 | 0.5 | NT | NT |
| Example 18 | OH | 13 | 0.1 | 0.1 | NT | NT |
| Example 17 | OH | 18.9 | 0.1 | 0.1 | NT | NT |
| Example 16 | OH | 32.2 | 0.2 | 0.2 | NT | NT |

NT = Not tested
ic = Intracolonic administration
po = Oral administration

The parent acid i.e. the compound of reference example 1 is inactive in both assays.

3) In Vivo Septic Shock Model: *C Parvum*/LPS Shock

Male CD-1 mice, 25–30 g (Charles River: Raleigh, N.C.), are injected intravenously (i.v.) with 100 μμ}g killed *C. Parvum* (Coparvax; Burroughs Wellcome, RTP, NC).Ten days later the mice are injected i.v. with 20 μμ}g *E. Coli* 026:B6 lipopolysaccharide (LPS; Difco Labs, Detroit, Mich.) in the presence of the analgesic butorphenol (150 μμ}g per mouse).

The test compounds are dissolved in dimethyl sulphoxide and diluted into 0.5% methyl cellulose and then dosed orally 2 hours before the LPS and at the same time as the LPS.

Results

| Compound (Oral Dose) | Alive/Total | % Survivors |
|---|---|---|
| Control | 0/8 | 0 |
| Example 9 (75 mg/kg) | 4/8 | 50 |
| Reference Example 1 (75 mg/kg) | 2/8 | 25 |

What is claimed is:

1. A process for preparing (E)-4-(1,3-bis(cyclohexylmethyl)-1,2,3,6-tetrahydro-2,6-dioxo-9H-purin-8-yl)cinnamic acid nonaethylene glycol methyl ether ester, said process comprising:
   a) reacting (E)-4-(1,3-bis(cyclohexylmethyl)-1,2,3,6-tetrahydro-2,6-dioxo-9H-purin-8-yl)cinnamic acid with N,N'-carbonyldiimidazole to prepare (E)-(1,3-bis(cyclohexylmethyl)-8-(4-(2-(1H-imidazol-1-ylcarbonyl) vinyl)phenyl)-9H-purin-2,6(1H, 3H) dione; and b) reacting (E)-(1,3-bis(cyclohexylmethyl)-8-(4-(2-(1H-imidazol-1-ylcarbonyl)vinyl)phenyl)-9H-purin-2,6(1H, 3H) dione with poly(ethyleneglycol) monomethyl ether to prepare (E)-4-(1,3-bis(cyclohexylmethyl)-1,2,3,6-tetrahydro-2,6-dioxo-9H-purin-8-yl)cinnamic acid nonaethylene glycol methyl ether ester.

2. A process for preparing a compound of formula (I):

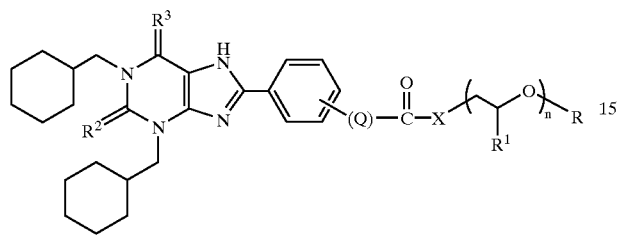

(I)

wherein:

X is —O— or —NH—;

Q is (—CH$_2$—)$_p$, (—CH=CH—)$_p$, (—C≡C—)$_p$ where p is an integer of from 0 to 4;

R$^1$ is hydrogen or methyl;

R$^2$ and R$^3$ independently represent O or S n is an integer of 1 to 50; and

R is hydrogen or methyl;

said process comprising:

a) reacting a compound of formula (II)

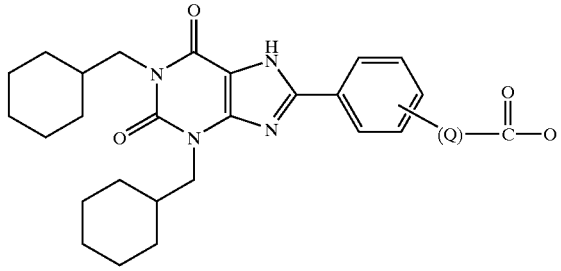

(II)

with N,N'-carbonyldiimidazole to prepare an acylimidazole intermediate and b) reacting the acylimidazole intermediate with a compound of formula (III)

(III)

to prepare the compound of formula (I).

* * * * *

UNITED STATES PATENT AND TRADEMARK OFFICE
CERTIFICATE OF CORRECTION

| | | |
|---|---|---|
| PATENT NO. | : 7,002,012 B2 | Page 1 of 1 |
| APPLICATION NO. | : 10/174414 | |
| DATED | : February 21, 2006 | |
| INVENTOR(S) | : Daluge et al. | |

It is certified that error appears in the above-identified patent and that said Letters Patent is hereby corrected as shown below:

On the title page item (54), and col. 1, line 4,
Should read:
(54) SUBSTITUTED (1,3-BIS(CYCLOHEXYLMETHYL)-1,2,3,6-TETRAHYDRO-2,6-DIOXO-9H-PURIN-8-YL)PHENYL DERIVATIVES, THEIR PREPARATION AND THEIR USE IN THE TREATMENT OF INFLAMMATORY CONDITIONS AND IMMUNE DISORDERS

Column 32, line 5
Should read:

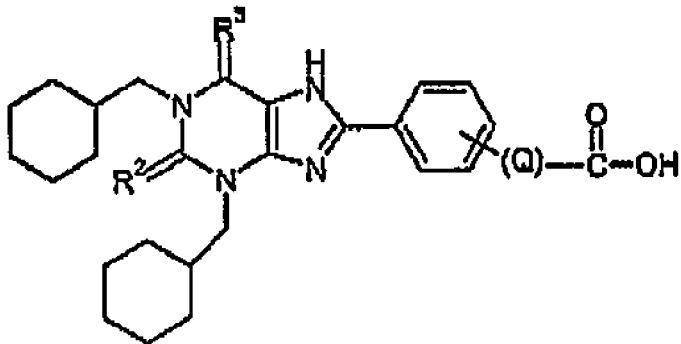

Signed and Sealed this

Eighth Day of May, 2007

JON W. DUDAS
*Director of the United States Patent and Trademark Office*